(12) United States Patent
Flickinger et al.

(10) Patent No.: US 11,298,159 B1
(45) Date of Patent: Apr. 12, 2022

(54) POLYAXIAL BONE PLATE AND LOCKING ASSEMBLY

(71) Applicant: Meditech Spine, LLC, Atlanta, GA (US)

(72) Inventors: Eric Flickinger, Atlanta, GA (US); Robert Bruce Dunaway, Akron, OH (US)

(73) Assignee: MEDITECH SPINE, LLC, Atlanta, GA (US)

( * ) Notice: Subject to any disclaimer, the term of this patent is extended or adjusted under 35 U.S.C. 154(b) by 0 days.

(21) Appl. No.: 17/141,424

(22) Filed: Jan. 5, 2021

(51) Int. Cl.
*A61B 17/70* (2006.01)
(52) U.S. Cl.
CPC ................................ *A61B 17/7059* (2013.01)
(58) Field of Classification Search
CPC .................. A61B 17/7059; A61B 17/80–8095
See application file for complete search history.

(56) References Cited

U.S. PATENT DOCUMENTS

| | | |
|---|---|---|
| 6,193,721 B1 | 2/2001 | Michelson |
| D440,311 S | 4/2001 | Michelson |
| 6,398,783 B1 | 6/2002 | Michelson |
| 6,416,528 B1 | 7/2002 | Michelson |
| 6,428,542 B1 | 8/2002 | Michelson |
| 6,454,771 B1 | 9/2002 | Michelson |
| 6,527,776 B1 | 3/2003 | Michelson |
| 6,592,586 B1 | 7/2003 | Michelson |
| 6,616,666 B1 | 9/2003 | Michelson |
| 6,620,163 B1 | 9/2003 | Michelson |
| 6,712,818 B1 | 3/2004 | Michelson |
| 6,916,320 B2 | 7/2005 | Michelson |
| 6,926,718 B1 | 8/2005 | Michelson |
| 6,936,050 B2 | 8/2005 | Michelson |
| 6,936,051 B2 | 8/2005 | Michelson |
| 6,969,390 B2 | 11/2005 | Michelson |
| 7,074,221 B2 | 7/2006 | Michelson |
| 7,074,255 B2 | 7/2006 | Michelson |
| 7,137,984 B2 | 11/2006 | Michelson |
| 7,625,381 B2 | 12/2009 | Michelson |
| 7,727,266 B2 * | 6/2010 | Lindemann ........ A61B 17/8042 606/289 |
| 8,486,115 B2 | 7/2013 | Fisher |
| 8,652,182 B1 * | 2/2014 | Walker ............... A61B 17/8052 606/296 |

(Continued)

OTHER PUBLICATIONS

U.S. Appl. No. 14/936,394, Non-Final Office Action, dated Dec. 8, 2017, 13 pages.

(Continued)

*Primary Examiner* — Nicholas J Plionis
(74) *Attorney, Agent, or Firm* — Kilpatrick Townsend & Stockton LLP

(57) ABSTRACT

A bone plate assembly includes a bone plate and a rotatable lock. The bone plate includes a superior surface, an inferior surface, and at least one screw through-hole that is configured to receive a bone screw. The bone plate includes a locking cavity that defined in the superior surface. The locking cavity includes a bottom surface that is recessed relative to the superior surface, and also includes a post that extends upwards from the bottom surface. The rotatable lock is supported on the post such that the rotatable lock is at least partially within the locking cavity.

17 Claims, 16 Drawing Sheets

(56) References Cited

U.S. PATENT DOCUMENTS

| | | | |
|---|---|---|---|
| 8,702,766 B2 | 4/2014 | Mueller | |
| 9,381,093 B1 | 7/2016 | Morris | |
| 9,730,804 B2* | 8/2017 | Cowan, Jr. | A61F 2/447 |
| 10,016,224 B2* | 7/2018 | Altarac | A61B 17/7059 |
| 10,064,666 B2 | 9/2018 | Dunaway | |
| 10,869,703 B2 | 12/2020 | Dunaway | |
| 2002/0147450 A1 | 10/2002 | LeHuec | |
| 2002/0188296 A1 | 12/2002 | Michelson | |
| 2004/0039387 A1* | 2/2004 | Gause | A61B 17/1735 606/86 B |
| 2005/0075633 A1* | 4/2005 | Ross | A61B 17/8033 606/280 |
| 2005/0137597 A1 | 6/2005 | Butler | |
| 2009/0062863 A1 | 3/2009 | Peppers | |
| 2012/0158068 A1 | 6/2012 | Humphreys | |
| 2013/0023936 A1 | 1/2013 | Altarac et al. | |
| 2013/0204300 A1 | 8/2013 | Michelson | |
| 2014/0066997 A1 | 3/2014 | Humphreys | |
| 2014/0277478 A1 | 9/2014 | Moore | |
| 2016/0095637 A1* | 4/2016 | Elsbury | A61B 17/7059 606/290 |
| 2016/0128746 A1* | 5/2016 | Dunaway | A61B 17/8042 606/246 |
| 2018/0103989 A1* | 4/2018 | Altarac | A61B 17/80 |
| 2018/0271571 A1* | 9/2018 | Johnson | A61B 17/8042 |

OTHER PUBLICATIONS

U.S. Appl. No. 14/936,394, Notice of Allowance, dated May 2, 2018, 5 pages.

U.S. Appl. No. 14/936,394, "Restriction Requirement", dated Sep. 19, 2017, 6 pages.

U.S. Appl. No. 16/103,734, Non-Final Office Action, dated Apr. 7, 2020, 16 pages.

U.S. Appl. No. 16/103,734, Notice of Allowance, dated Aug. 28, 2020, 9 pages.

U.S. Appl. No. 16/685,836, Non-Final Office Action, dated Oct. 28, 2021, 16 pages.

* cited by examiner

POLYAXIAL BONE PLATE AND LOCKING ASSEMBLY

FIELD OF INVENTION

This application relates to implantable internal fixator assemblies for use in stabilizing and supporting the spine.

BACKGROUND OF THE INVENTION

Broken bones heal naturally, albeit slowly compared to most soft tissue, provided they are adequately supported and relieved of stress. In a simple break in an extremity, adequate support and relief may be provided from outside the body with a device as simple as a splint or a cast, which immobilizes the body part containing the broken bone. Such procedures may suffice when the bone can be set and will retain its position without significant intervention, for instance when the break is simple and contained in a body part that can be readily immobilized in a natural posture. Immobilization is also therapeutic to treat damage to connective tissue, by preventing repetitive stress and further injury to, for instance, damaged ligaments, tendons, or cartilage.

When a break or fracture is in the spine, or when the connective tissue between one or more vertebrae is damaged, external immobilization is significantly less effective for several reasons. Because the spine is the central support column of the human body, externally imposed immobilization is impractical, as it involves immobilizing most of the body. Furthermore, the spine is a load-bearing structure that is subject to repetitive compressive and rotational stresses constantly during the normal waking life of a person; therefore, external immobilization of the spine significantly impacts the mobility and activity of a patient. For practical purposes, externally imposed spinal immobilization often requires that the patient is subjected to bed rest, is wheelchair-bound, is fitted with a significant amount of uncomfortable stabilizing equipment, or a combination of the above.

Since the advent of sterile surgery, it has been possible for doctors to internally stabilize broken bones and connective tissue with implants. Internal stabilization can be complex, but tends to allow much greater precision in aligning broken bones, and significantly reduces misalignment in healing. Internal stabilization also improves healing time and allows a patient to live a much more normal life while still healing. One such type of implant is a bone plate, which is a shaped rigid or semirigid part usually having several through-holes by which a surgeon will attach the plate to parts of a broken bone, or to parts of two or more proximate bones that require alignment, by means of screws. All such parts are formed of biocompatible materials and may either be left in the body during and after healing, or may be removed after healing. Ideally, bone plates would be painstakingly formed and attached in several directions, so that the plate would conform perfectly to the patient's body, and would be secured to the bone or bones with an optimal balance of minimal tissue damage and maximal rigidity. In practice, the fact that such devices must be attached in surgery restricts the amount of time and the amount of access to the bone, such that physicians require such devices to attach efficiently and primarily from one direction.

Another significant challenge to the use of bone plates is the stress placed on the bone by the tightening of the bone screws. Ordinary screws in other fields may be held fast to a surface by the friction between the screw head and the outer surface of the attached part, by friction between the screw threads and the material, or a combination. However, the force generated by tightening screws to achieve such friction in bone may cause excessive damage, and the healing of the bone over time in combination with the motion of the body may act to gradually force the bone screw from its position. Therefore, bone plate implants may require an assortment of apparently contradictory features including but not limited to additional locks to prevent the extrusion of the bone screw from the bone and plate, attachment that is both secure and that provides some wiggle-room, attachment that is very quick but also very secure or conforming, and/or other features.

Anti-backout mechanisms on bone plates tend to suffer a variety of drawbacks. Parts of conventional anti-backout mechanisms, for instance screws and washers, tend to be small and delicate, and can be broken during installation or lost by the surgeon within the surgical wound. In conventional bone plates that possess internal anti-backout mechanisms, securing the mechanism may require specialized tools, or it may be difficult to ascertain whether the anti-backout mechanism has been fully engaged.

BRIEF SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Improved bone plates and locking assemblies for immobilizing vertebral bodies in the spine are disclosed herein. The plate is installed in one or more vertebrae with bone screws through a plurality of through-holes in the plate, which are then secured by a locking element or locking assembly. Specifically, the disclosed bone plates and locking assemblies are both secure and capable of rapid installation, being designed for ease of installation and use, with minimal moving parts that could potentially become broken or lost within the surgical wound during installation.

According to certain embodiments, a bone plate assembly includes a bone plate and a rotatable lock. The bone plate includes a superior surface, an inferior surface, at least one screw through-hole configured to receive a bone screw, and a locking cavity defined in the superior surface. The locking cavity may include a bottom surface that is recessed relative to the superior surface, and may also include a post extending upwards from the bottom surface. The rotatable lock may be supported on the post and may be rotatable while supported on the post.

According to some embodiments, a bone plate assembly includes a bone plate and a lock. The bone plate includes a superior surface, at least one screw through-hole configured to receive a bone screw, a blind locking cavity defined in the superior surface, and a post within the locking cavity. The lock may be supported on the post such that the lock is at least partially within the locking cavity.

According to various embodiments, a bone plate assembly includes a bone plate, and the bone plate includes a superior surface, an inferior surface, and at least one screw through-hole configured to receive a bone screw. The bone plate also includes a locking cavity defined in the superior surface. The locking cavity may include a bottom surface that is recessed relative to the superior surface, a sidewall surface extending from the bottom surface to the superior surface, and a post within the locking cavity. The locking cavity may also include a locking feature extending from the sidewall surface into the locking cavity.

Various implementations described herein can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

DETAILED DESCRIPTION OF THE INVENTION

Figure 1:
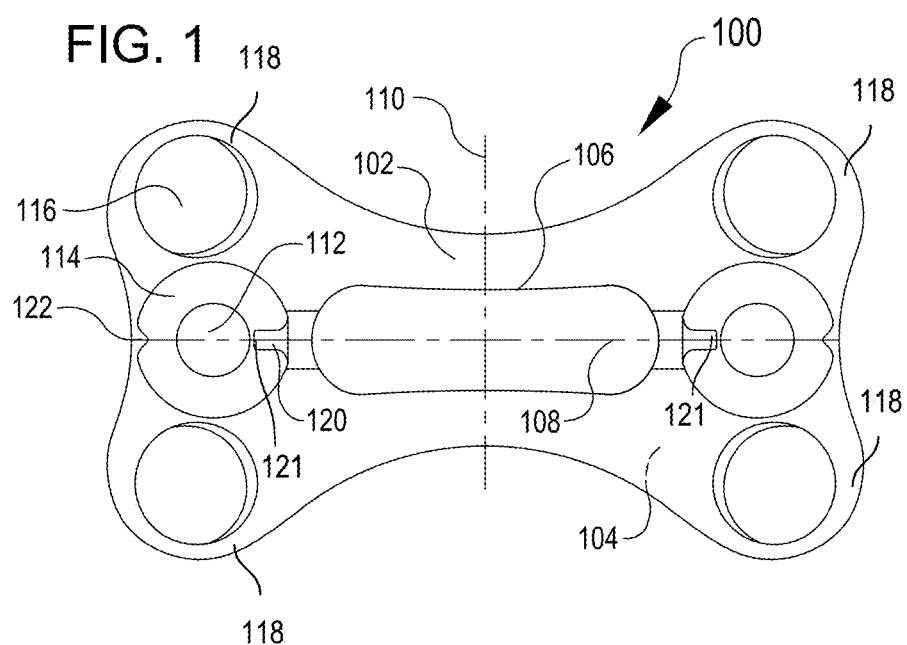
FIG. 1 is a top view of a bone plate according to an example.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

This patent discloses polyaxial bone plates and locking mechanisms that are configured for immobilization of vertebral bodies via fixation to surfaces thereof, with features for preventing screw backout while minimizing certain risks and the time required for surgical installation.

As shown in the Figures, a bone plate includes a plurality of through-holes for receiving bone screws. In a polyaxial bone plate, the through-holes are configured to seat bone screws in a variety of directions. The locking mechanisms disclosed herein may be applied to monoaxial or polyaxial bone plate designs. The locking mechanisms are configured to partially obstruct a region above at least a portion of the head of a bone screw and prevent the screw from inadvertently backing out of the through-hole. In some cases, the locking mechanism includes a plate and a lock, which may be one or multiple parts including a shaft, one or more locking features that restrain movement of the locking mechanism, and a noncircular head element that cooperates with the screw heads to form the partial obstruction described above. When assembled with the bone plate, the lock is seated in a through-hole or bore in the bone plate adjacent to one or more of the screw through-holes. As illustrated, the lock sits adjacent to and between two screw through-holes; however, a lock may be configured to secure one, two, or more than two screws without deviating from the design principles herein disclosed. Any part herein disclosed may be composed of any material or combination of materials that is biocompatible and sufficiently rigid to perform the part's function.

In some embodiments, a bone plate assembly includes a bone plate having at least one screw through-hole and a locking cavity. In certain cases, the locking cavity has a bottom surface that is recessed relative to a superior surface of the locking cavity, and may also include a post extending upwards from the bottom surface. A lock may be rotatably supported on the post and at least partially within the locking cavity. In some embodiments, the bone plate assembly with the bone plate having the post may reduce the number of parts needed to assemble the bone plate assembly, may reduce the number of moving parts on the bone plate assembly, and/or may provide a location with improved strength for supporting the lock and allowing for rotation of the lock.

FIG. 1 shows a bone plate 100 from a top view, with the superior surface 102 visible. The opposing inferior face 104 is configured to attach to two or more vertebrae by a plurality of bone screws that are each inserted through a through-hole 116 of the bone plate 100. Bone plate 100 includes four through-holes 116 for bone screws, disposed in the lobes 118 of the bone plate 100 at the corners. The through-holes 116 for bone screws may be oriented in a polyaxial configuration to better contact and secure the bone plate 100 to vertebral bodies, and may be configured to permit a limited degree of freedom of motion of the bone screws once installed. One form of a polyaxial configuration can include tilting the through-holes 116 with respect to the long axis 108 of the bone plate 100, such that bone screws inserted therethrough would point inward toward one another, or alternatively outward away from one another. Another form of a polyaxial configuration can include tilting the through-holes 116 with respect to the short axis 110 of the bone plate 100. In some cases, the through-holes 116 can be oriented in a symmetrical arrangement or in an asymmetrical arrangement relative to one another, and each through-hole 116 may be tilted along one or both of the long axis 108 and the short axis 110. An additional form of a polyaxial configuration can include providing sufficient clearance between the through-holes 116 and the associated bone screws that the screws can be seated in the through-holes at various angles of entry according to a medical need, as determined by a physician performing the installation. As described in more detail below, a lock 300 (FIG. 3) is designed so that it does not radially impinge the bone screws and so that it allows a degree of freedom of movement as the screw threads seat in the bone and as the bone heals around them.

Bone plate 100 also includes one or more bores 112 for receiving the lock 300 (FIG. 3) that are located between the through-holes 116 for the bone screws. Each of the bores 112 has a counter-bore 114 on the superior surface and one or more surface features 120, 122 disposed within the counter-bore 114 that are configured to interact with the locking ring 200 (FIG. 2) and/or the lock 300 (FIG. 3), as described in more detail below. In some cases, a second counter-bore (not shown) is included on the inferior face 104 around the bore 112 for accommodating the attachment of the lock 300 (FIG. 3).

Figure 2:
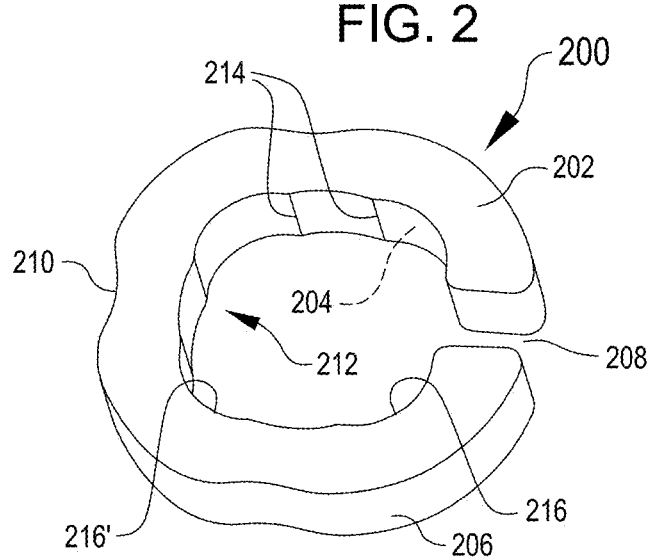
FIG. 2 is a perspective view of a locking ring configured to be received by the bone plate of FIG. 1.
Figure 3:
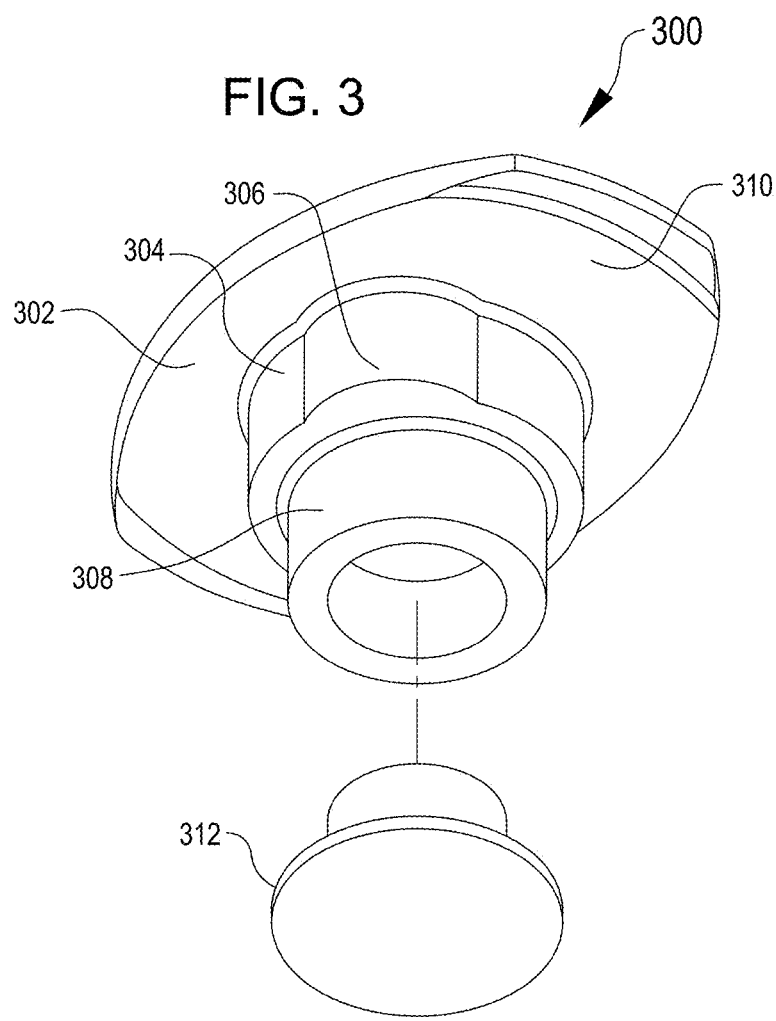
FIG. 3 is perspective view of a lock configured to be received by the bone plate and locking ring of FIGS. 1 and 2, respectively.

As shown in FIG. 1, the counter-bore 114 in the superior surface 102 of the bone plate 100 surrounds the bore 112 and has two surface features, a large surface feature 120 and a small surface feature 122 extending upward for interacting with a locking ring 200 (FIG. 2) and a lock 300 (FIG. 3). In some embodiments, the stop 121 is the surface feature 1212, although in other embodiments, the surface feature 120 may be other features as desired. The large surface feature 120 extends toward the superior surface 102 from the counter-bore 114. This large surface feature 120 may also be herein referred to as a rotational stop. Opposite from the rotational stop 121, the counter-bore 114 has a smaller surface feature 122 that extends into the counter-bore 114 for helping secure the locking ring 200 (FIG. 2). In some cases, the surface features 120, 122 are oriented opposite one another and along the long axis 108, but in other cases, the surface features 120, 122 can have other orientations, such as parallel to the short axis 110 of the bone plate 100.

FIG. 2 shows a locking ring 200 configured for use with a bone plate such as the bone plate 100 shown in FIG. 1. The locking ring 200 is a generally circular element with at least one retention feature, which may include a break 208 and a notch 210, such that the locking ring 200 can elastically deform when subjected to a radial load. The locking ring 200 is sized and shaped to fit within the counter-bore 114 on the superior surface 102 of the bone plate 100, and is oriented such that the break 208 rests about the larger surface feature 120, and the notch 210 fits about the smaller surface feature 122. The notch 210 alters the elastic stiffness of the locking ring, and the depth and width of the notch 210 can be varied to tune the stiffness. In an unflexed position, the locking ring 200 may sit in contact with one or more of the surface features 120, 122 and in contact with the surface of the counter-bore 114, but cannot freely rotate from its original orientation. The interior radial surface 212 of the locking ring 200 may be non-cylindrical, having concave depressions 216, 216' situated at regular intervals with small peaks 214 between them, which may be disposed at various increments about the interior surface, for example, at approximately 45-degree increments. The locking ring 200 may also have depressions or surface features in the outer radial surface that may be configured to alter the stiffness of the locking ring. The interior concave depressions 216, 216' in the locking ring 200 may have different depths in an alternating fashion, although they need not. Alternatively, the interior radial surface 212 of the locking ring 200 may have concave depressions situated at approximately 90-degree increments about a cylindrical radial surface, or it may have an irregular internal radius with local maxima disposed at intervals, for example approximately 90-degree or 45-degree intervals.

FIG. 3 shows a lock 300 that is configured to mate with a bone plate such as the bone plate 100 shown in FIG. 1 and with a locking ring such as the locking ring 200 shown in FIG. 2. Lock 300 includes a generally oval head section 302 with an overhang 310, a circular connecting shaft 308, and a shoulder 304 disposed between the head section 302 and the shaft 308. When the lock 300 is assembled with the bone plate 100, the shoulder 304 abuts the surface of the counter-bore 114, and the circular shaft 308 is configured to fit within the bore 112 at the center of the counter-bore 114, passing through to the inferior surface of the bone plate 100. The circular shaft 308 is connected to the bone plate 100 by rotatable attachment with the bore 112. In some cases, the circular shaft 308 is hollow along a part of its length, such that the shaft end distal from the head may be widened and the shaft may act as a rivet. In some cases, the connection between the lock 300 and the bone plate 100 is permanent and is achieved before the bone plate 100 is implanted. Effective connection may be achieved by riveting or by any comparable means, which may or may not be permanent. Alternative methods of permanent or semi-permanent attachment between the lock 300 and the bone plate 100 are possible within the scope of the invention; for example, an optional end cap 312 may be installed abutting the lower surface of the lock shaft using threads, welding, an interference fit, or other suitable ways of attachment. The shoulder 304 of the lock 300 also includes a locking feature, for example, radial feature 306, which may be an oval shape, semicircular protrusions, or any other suitable positive radial feature, and which is configured to abut one or more concave depressions 216, 216' of the interior radial surface 212 of the locking ring 200 (FIG. 2).

Figure 4:
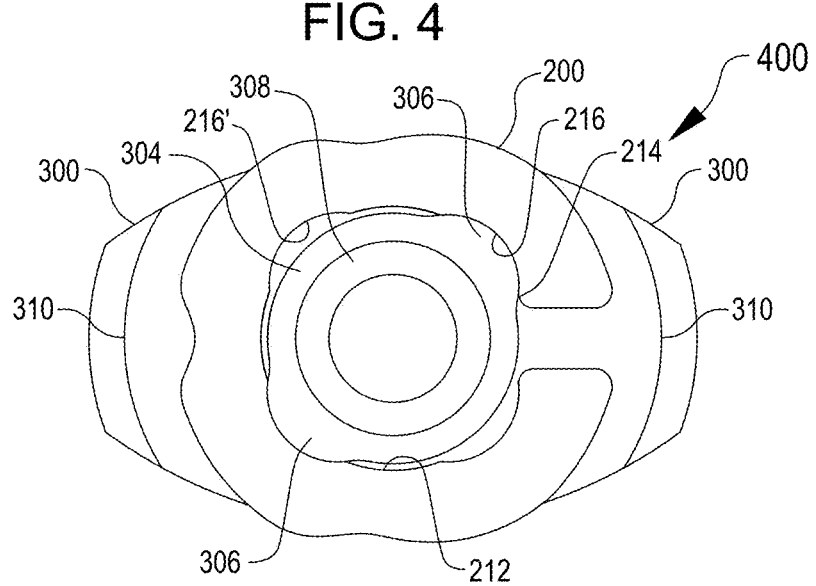
FIG. 4 is a bottom view of the lock of FIG. 3, shown assembled with the locking ring of FIG. 2.

FIG. 4 shows a bottom view of the lock 300 (FIG. 3) assembled with the locking ring 200 (FIG. 2), showing the relative positioning of the overhang 310 of the lock 300, circular shaft 308, shoulder 304, and locking ring 200. The radial feature 306 of the noncircular shoulder 304 is shown resting in a first concave depression 216 of the locking ring 200. The radial feature 306 is shaped such that, when the lock 300 is turned within the locking ring 200, the radial feature 306 contacts the interior radial surface 212 of the locking ring 200, causing it to flex outwardly as the lock turns, until the radial feature 306 comes to rest in a second concave depression (e.g., second concave depression 216') in the locking ring 200 and the locking ring 200 returns to its unflexed shape. In this non-limiting example, the noncircular shoulder 304 has two radial features 306, each disposed in a concave depression 216 in the locking ring 200. The lock 300 is shown in its unlocked position relative to a bone plate such as bone plate 100 shown in FIG. 1. From this position, the lock 300 may be rotated (counterclockwise from below as in the view of FIG. 4, although clockwise when viewed from above) 90 degrees until the lock 300 is secured in the locked position. During rotation, the locking ring 200 will deform elastically as the radial feature 306 of the noncircular shoulder 304 of the lock 300 presses outwards on the interior of the locking ring 200, and then the locking ring 200 will return to its unflexed position when the lock 300 has passed fully to its locked position. In some cases, the lock passes through 90 degrees of rotation from its unlocked to its locked position, but other configurations are possible by adding additional convex and concave features to the noncircular shoulder 304 and locking ring interior radial surface 212.

The curved interior radial surface 212 of the locking ring 200 is shaped to exert at least some rotational force on the lock 300 when the lock 300 is oriented between the locked and unlocked positions, such that the lock 300 will provide tactile feedback to a user, such as a surgeon turning the lock 300 while installing the apparatus in a patient. The combination of the curvature and elastic deformation of the locking ring 200 will exert a circumferential force on the lock 300 resisting an initial turning force when a surgeon begins to turn the lock from its unlocked position. When the lock 300 has been turned to a position sufficiently close to the locked position, which in this non-limiting example is approximately ninety degrees, the curvature of the locking ring 200 in combination with the elastic deformation of the locking ring 200 will exert a circumferential force serving to "snap" the lock 300 into the locked position.

The locking ring 200 is configured to have a spring stiffness such that the lock 300 may be operated by a physician during surgery without requiring substantial mechanical advantage or putting excessive strain on the underlying bone to which the bone plate may be attached. In some cases, the target stiffness is such that the lock 300 can be turned by hand using an inline screwdriver, providing enough rotational force that it provides tactile feedback along the screwdriver to a surgeon performing the installation. Furthermore, the lock 300 can be configured to accept a driver bit, which may be a standard hex bit, star bit, Torx® bit, or other common variety of driver bit. The lock 300 may also be configured to accept the same driver bit as bone screws, further improving the simplicity of installation of the apparatus.

In some non-limiting examples, the lock 300 is configured to interact with the larger of the two positive surface features (or the "stop") 120 of the counter-bore 114 (FIG. 1). In some cases, the lock 300 is restricted to a partial arc of rotation by the radial feature 306 of the noncircular shoulder 304 encountering the positive surface feature 120 (e.g., stop 121). For example, when the lock 300 is in the unlocked position, the radial feature 306 abuts the stop 121, such that the lock 300 can only be turned toward the locked position—that is to say, only in one direction. Likewise, when the lock 300 is in the locked position, it can only be turned toward the unlocked position, which will be in the opposite direction. This binary configuration of the lock aids in preventing operator error in locking or unlocking the apparatus. In some non-limiting examples, there are two radial features 306 in the form of protrusions from the noncircular shoulder 304 arranged symmetrically and opposite, such that a different protrusion abuts the stop 121 in the locked position than in the unlocked position. In the illustrated examples, the stop 121 and radial features 306 are sized such that the lock 300 may rotate approximately 90 degree, but a configuration could be readily achieved that would restrict the rotation of the lock to a different arc, such as 60 degrees, 45 degrees, 30 degrees, or other arcs. In configurations having a symmetrical noncircular section, the effect of said symmetry is that net radial loading when the lock 300 passes between the unlocked and locked positions is minimized, reducing wear on the lock and minimizing the possibility of breakage.

Figure 5A:
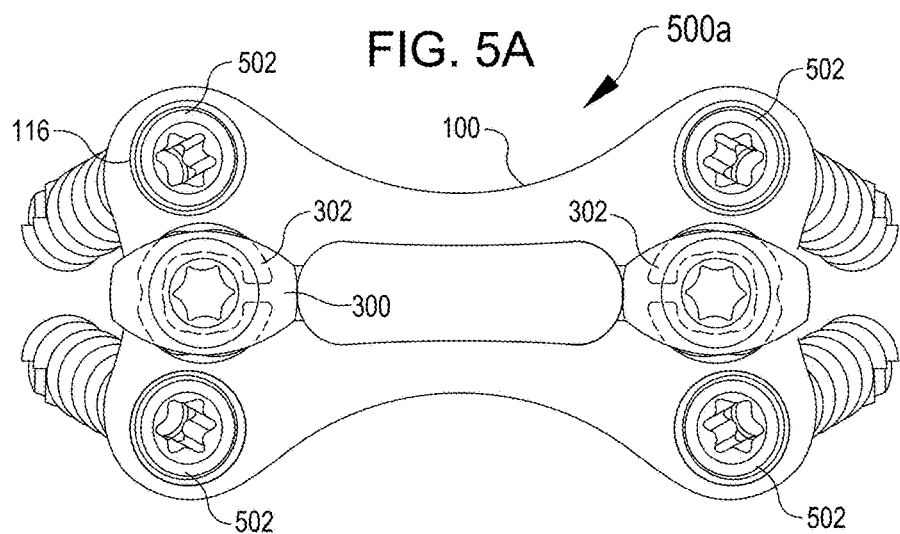
FIG. 5A is a top view of an assembled apparatus including a bone plate, a locking ring, a lock, and bone screws, shown in the unlocked position.

FIG. 5A shows an assembled bone plate apparatus 500a from a top view, including bone plate 100, bone screws 502 inserted in through-holes 116, and locks 300 seated on locking rings 200 (shown in broken lines where obstructed by the locks 300) of FIGS. 1-4, with each of the locks 300 in the unlocked position. The bone screws 502 are arranged in a polyaxial configuration, and no part impinges on the screw heads. In particular, the head sections 302 of the two locks 300 are oriented away from the through-holes 116 so as not to overhang the bone screws 502. The bone plate 500a and locking ring 200 have points of minimum and maximum clearance 504 and 506 between each locking ring 200 and a boundary of the counter-bore 114. In some cases, the locking ring 200 may be in contact with the counter-bore 114 at a point of minimum clearance 504, and may have a clearance of approximately 0.2 mm radially at a point of maximum clearance 506. In some cases, the maximum clearance can vary to approximately 0.3 mm, or up to approximately 0.75 mm, or any other suitable distance.

Figure 5B:
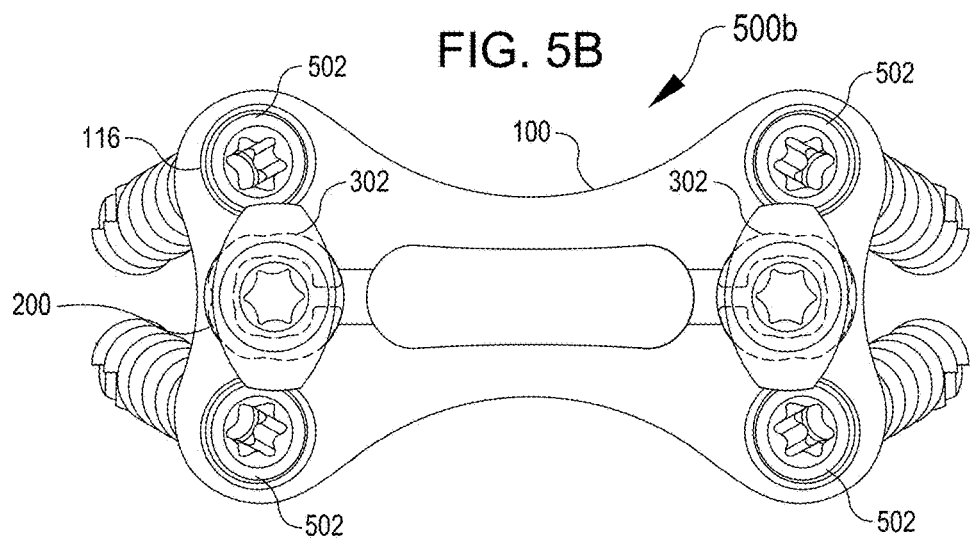
FIG. 5B is a top view of the assembled apparatus of FIG. 5A, shown in the locked position.

FIG. 5B shows the assembled bone plate apparatus of FIG. 5A, with the locks 300 in the locked position 500b. Here, the oval head sections 302 of the two locks 300 lie above and partially obstructing the removal path of the bone screws 502, preventing backout. In some cases, the locks 300 are designed to clear the bone screws 502 such that the locks do not impinge on the bone screws 502. By providing a slight clearance between the locks 300 and the bone screws 502, the screws are permitted to toggle and settle, which in some configurations may be preferred over having fully rigid attachment. The configuration shown provides that, when the bone screws 502 are fully inserted and the locks 300 are in the locked position, the bone screws 502 do not exert an axial load on the locks 300, although gradual settling and toggling of the screws may initiate contact between screw heads and locks.

Figure 6:
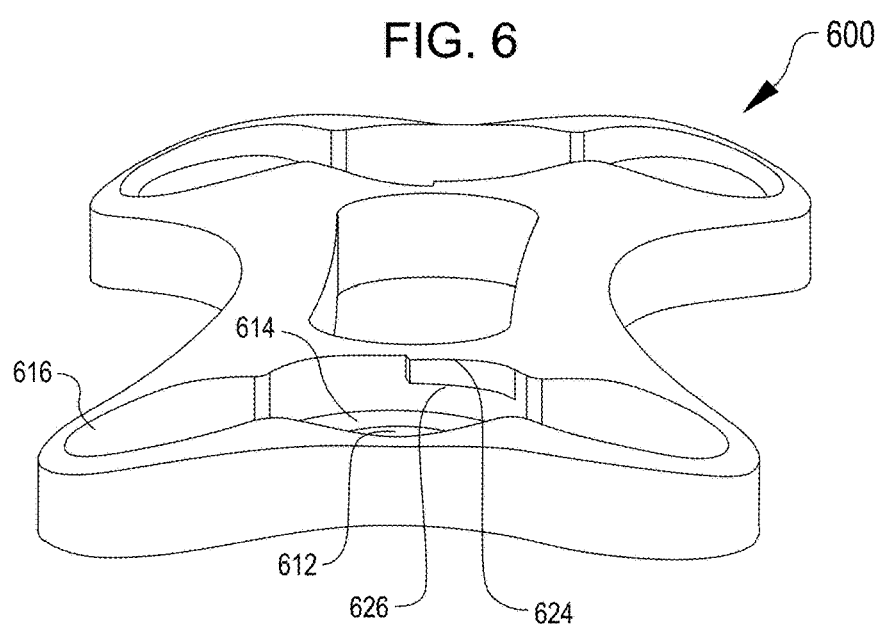
FIG. 6 is a perspective view of a bone plate according to a second example.
Figure 7:
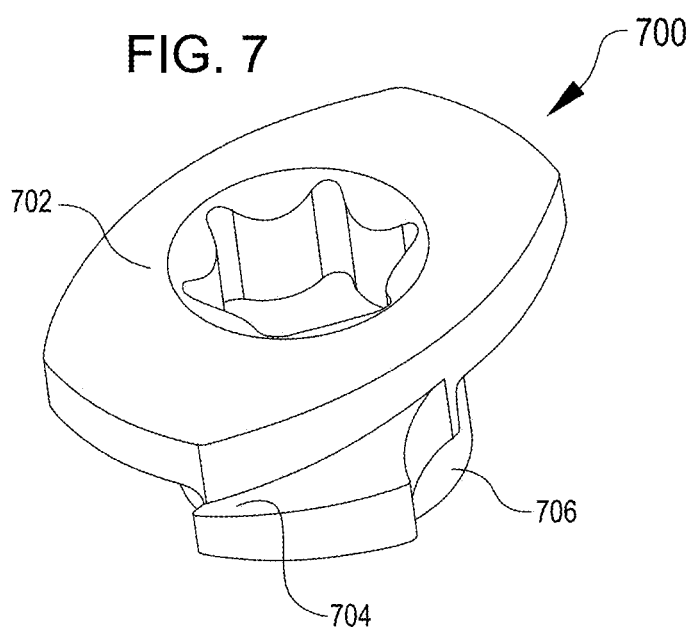
FIG. 7 is a perspective view of a lock configured to be received by the bone plate shown in FIG. 6.

FIG. 6 shows a polyaxial bone plate 600, from a perspective view, having an alternative structure within the counter-bore 614. The alternative structure is an extension 624 of the counter-bore wall, extending into the cylindrical space of the counter-bore 614 and creating a radial undercut 626 along a side of the counter-bore that is designed to mate with a positive radial feature 704 of an alternative lock 700 (FIG. 7). In this example, each counter-bore 614 possesses only a single extension 624 and radial undercut 626, although each counter-bore may include multiple radial undercut features for matching with positive radial locking elements of alternative locks. The radial undercut 626 narrows in a wedge fashion such that a lock 700 (FIG. 7) may be inserted in an unlocked position and secured in a rotatable fashion to the bone plate 600, such that it can be rotated into a locked position. As with bone plate 100, the bone plate 600 has at least one through-hole 616 for bone screws adjacent to each counter-bore 614, and a lock through-hole 612 is arranged in the counter-bore 614.

FIG. 7 shows a lock 700 configured to mate with the bone plate 600 (FIG. 6). As described above, the lock 700 includes a locking feature, for example, positive radial feature 704 that is configured to mate with the radial undercut 626 of the counter-bore 614 (FIG. 6). In this example, no additional locking ring part is needed to create the locking action. Assembly of the apparatus as shown may be achieved by assembling the lock 700 into the lock through-hole 612 of the bone plate 600 and attaching the shaft 706 to the lock through-hole 612. The lock 700 and bone plate 600 can be rotatably attached together as described above with reference to the bone plate 100 and lock 300 (FIGS. 1, 3, and 5). The unlocked and locked positions may be achieved by rotating the lock 700 until the positive radial feature 704 interacts with the radial undercut 626 (FIG. 6) in the form of a taper lock. Thus, both the receiving space formed by the radial undercut 626 and the positive radial feature 704 of the lock may have a slight taper in a circumferential direction, such that friction between the inner surface of the radial undercut 626 and the outer surface of the positive radial feature 704 of the lock 700 will act to retain the lock 700 in the locked position. The inner surface of the radial undercut 626 (FIG. 6) also performs the function of a stop, such that the lock can no longer rotate in the locking direction once locked. The lock may be prevented from rotating unnecessarily in the unlocking direction by interaction between the positive radial feature 704 and the counter-bore 614. Additional structures may be included in the counter-bore that form a stop, such as an optional protrusion, or alternatively, no stop may be provided. Alternatively, the radial undercut 626 or the positive radial feature 704 may include one or more additional surface features configured to increase resistance to turning, for instance, rough or jagged surfaces, a positive feature and groove, two interacting ratcheting surfaces, or other similar features.

Figure 8A:
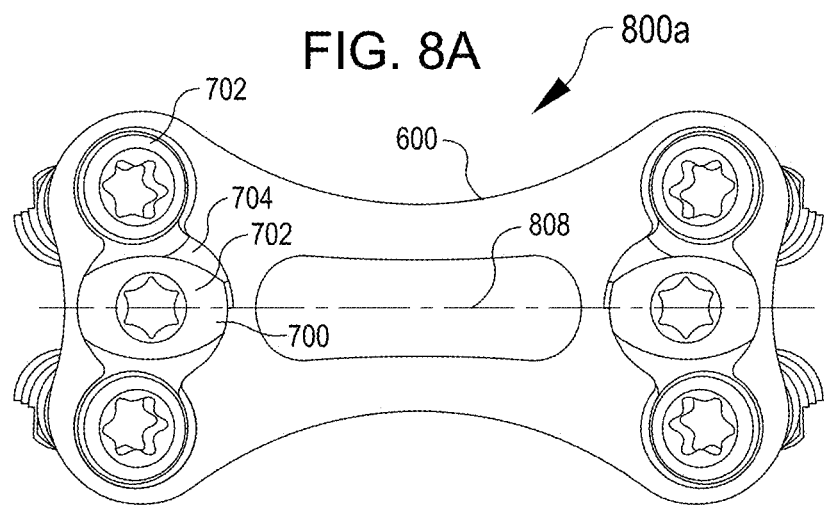
FIG. 8A is a top view of an assembled apparatus including the bone plate of FIG. 6 and the lock of FIG. 7, with bone screws, shown in the unlocked position.

FIG. 8A shows a bone plate assembly in an unlocked position 800a, from the top view, including a bone plate 600, locks 700, and bone screws 802, as shown in FIGS. 6 and 7. As shown, the locks 700 are oriented in the unlocked position. The bone screws 802 are arranged in a polyaxial configuration, and no part impinges on the screw heads. In particular, the oval head sections 702 of the two locks 700 shown are oriented in line with the long axis 808 of the bone plate 600 such that no parts of the head sections 702 overlap with a region above any bone screw 802.

Figure 8B:
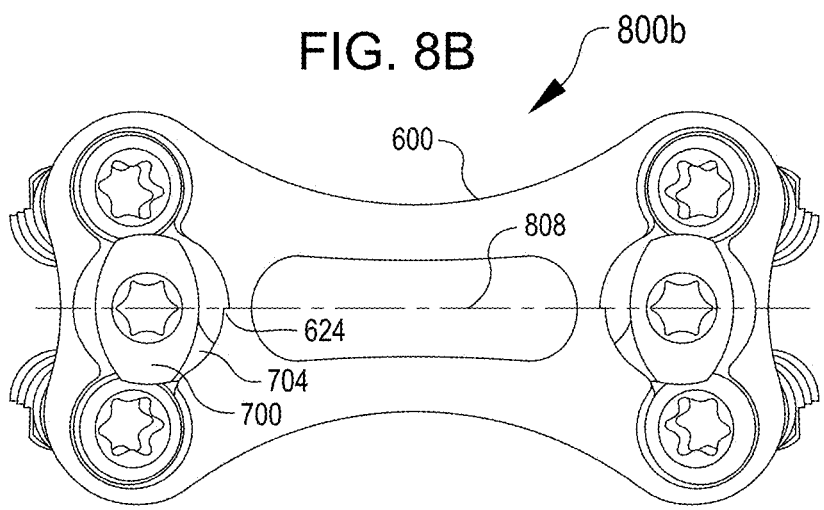
FIG. 8B is a top view of the assembled apparatus of FIG. 8A, shown in the locked position.

FIG. 8B shows a locked bone plate assembly 800b with the locks 700 oriented in the locked position. In the view shown, both locks 700 have been rotated approximately ninety degrees (albeit in opposite directions) relative to the configuration of FIG. 8A, such that the positive radial feature 704 of each lock 700 has become trapped as in a taper lock by the cavity of the radial undercut 626 (FIG. 6) formed by the extensions 624 in each counter-bore wall. When locked, friction between the radial undercut 626 and the positive radial feature 704 resists rotation, such that ordinary motion within a patient's body will not dislodge the lock 700. The resistance may be tuned by adjusting the taper of the undercut 626 and positive radial feature 704, or by the provision of additional locking features on one, the other, or both surfaces as described above. In the locked position, the head sections 702 of the locks 700 obstruct regions above the bone screws 802 in order to prevent screw backout. The locking directions that each of the two locks 700 must be turned may be the same or different; and the plate 600 may be rotationally symmetrical instead of mirror-symmetrical (as shown), in which case the locks could rotate identically in order to lock.

Figure 9:
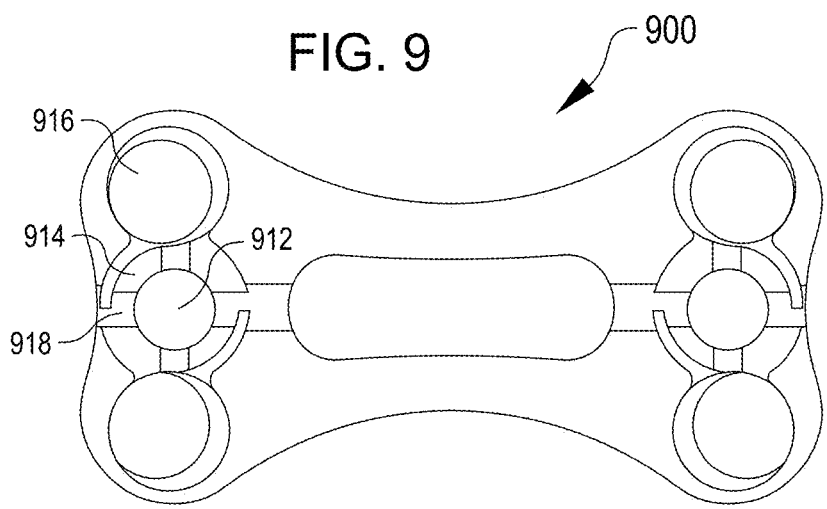
FIG. 9 is a top view of a bone plate according to a third example.
Figure 11:
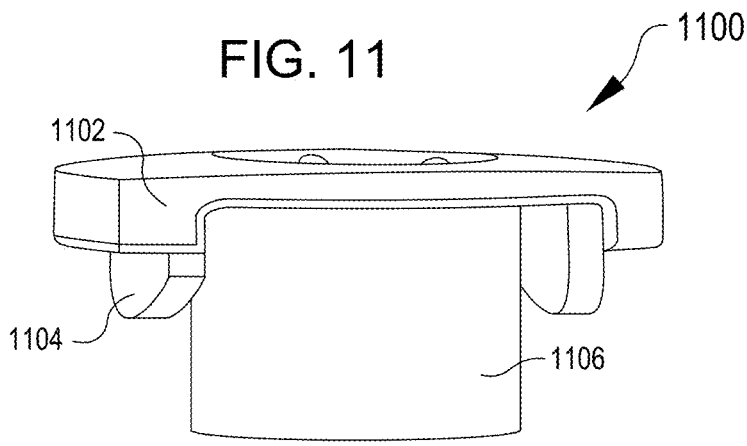
FIG. 11 is a perspective view of a lock configured to be received by the bone plate of FIGS. 9-10.

FIG. 9 shows a bone plate 900 from a top view that is configured to mate with a lock 1100 (FIG. 11). As with the bone plates described above, the bone plate 900 also includes counter-bores 914, concentric with lock through-holes 912 for receiving the lock 1100 (FIG. 11). The lock 1100 has positive, downwardly-directed positive protrusions 1104 (FIG. 11) that are sized and spaced to mate with grooves 918 in the counter-bore 914 radiating from the lock through-hole 912. The counter-bores 914 are adjacent to at least one bone screw through-hole 916.

Figure 10:
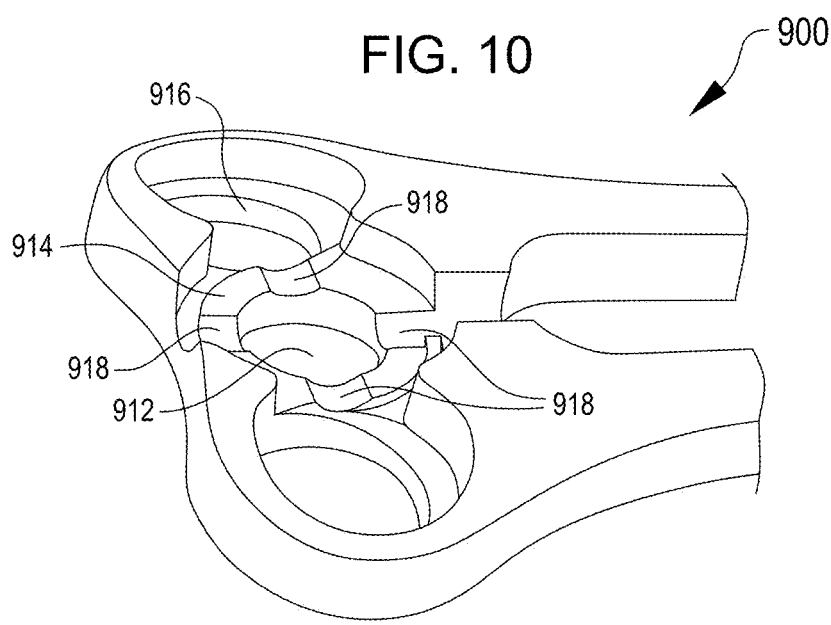
FIG. 10 is a perspective view of the bone plate of FIG. 9.

FIG. 10 shows the bone plate 900 of FIG. 9 in a perspective view, showing in more detail the surface features of the counter-bore 914. The counter-bore 914 possesses an interior surface that has a series of grooves 918 radiating from the lock through-hole 912, at set circumferential spacing. In this example, four grooves 918 are disposed at approximately 90 degree increments. The grooves 918 are configured to mate with downwardly-directed positive protrusions 1104 on the underside of an oval head section 1102 of a lock 1100 (FIG. 11).

FIG. 11 shows a lock 1100 configured for assembly with the bone plate 900 of FIGS. 9 and 10. Lock 1100 includes an oval head section 1102, and a locking feature including two positive protrusions 1104 extending downward from the oval head section 1102, and a shaft 1106. The two positive protrusions 1104 extend downward to mate with the grooves 918 of the counter-bore 914 (FIGS. 9 and 10), such that the lock 1100 can be stably seated within the grooves 918 with minimal tension in the shaft 1106. When rotated between the grooves 918, the positive protrusions 1104 press against the surface of the counter-bore 914 and produce axial tension in the shaft 1106 and/or bending stress in the oval head section 1102. Slight deformation may occur in the lock 1100 when the lock 1100 is rotated through intermediate positions where the positive protrusions are in-between the grooves 918. The positive protrusions 1104 possess curved surfaces where the lock 1100 interacts with the grooves 918 of the counter-bore, such that the lock 1100 resists rotation when the positive protrusions 1104 are seated in a groove 918, and such that the lock may "snap" into place when the lock is rotated such that the positive protrusions 1104 enter a groove 918.

Figure 12:
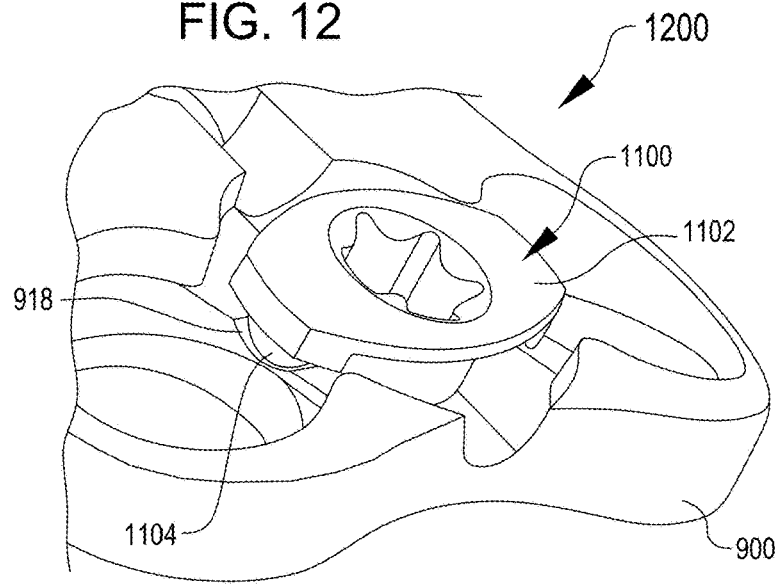
FIG. 12 is a perspective view of an assembled apparatus including the bone plate of FIGS. 9-10 and the lock of FIG. 11, shown in the locked position.

FIG. 12 shows a partially assembled, locked bone plate apparatus 1200 including lock 1100 and bone plate 900 in accordance with FIGS. 9-11, with the lock assembled in the bone plate 100 and rotated into the locked position. In this non-limiting example, the lock 1100 is permanently or semi-permanently attached into the lock through-hole 912 (FIGS. 9-10) in the bone plate 900. In this view, a positive protrusion 1104 extending from the underside of the oval head section 1102 of the lock 1100 is visible resting within a groove 918 of the underlying surface of the counter-bore 914.

Figure 13A:
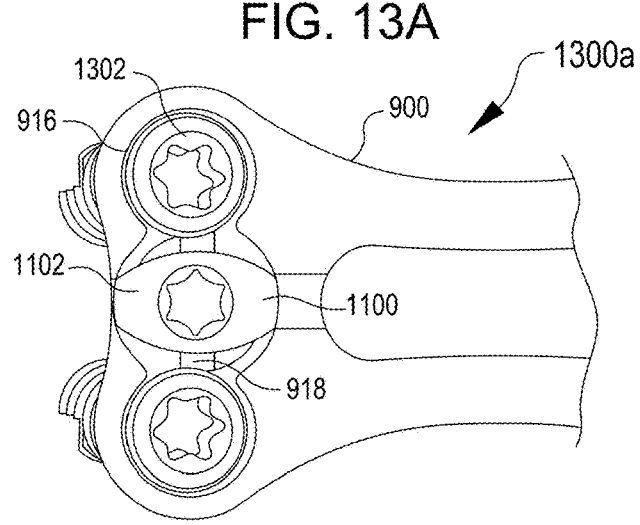
FIG. 13A is a top view of the assembled apparatus of FIG. 12, with bone screws, shown in the unlocked position.

FIG. 13A shows an unlocked bone plate assembly 1300a including the bone plate 900 and lock 1100 shown in FIG. 12, with bone screws 1302 in the at least one bone screw through-hole 916. As in previously described examples, the oval head section 1102 in the unlocked position does not interfere with the bone screws 1302.

Figure 13B:
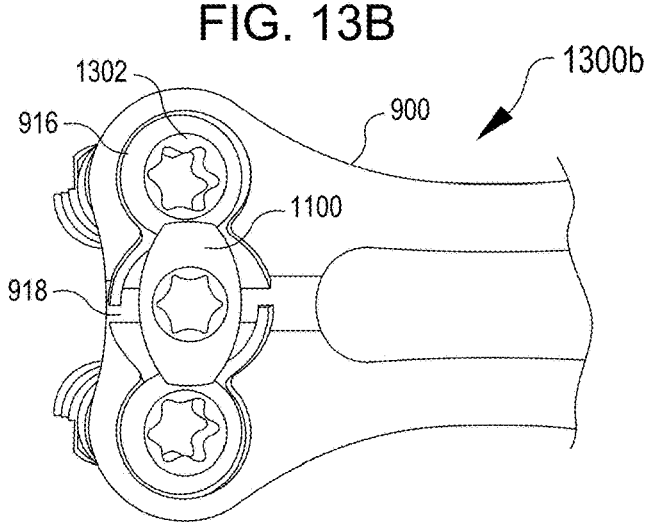
FIG. 13B is a top view of the assembled apparatus of FIG. 13A, shown in the locked position.

FIG. 13B shows a locked bone plate assembly 1300b based on locking the assembly 1300a shown in FIG. 13A. As in previously described examples, the oval head section 1102 in the locked position partially projects above the region above one or more of the bone screws 1302 without contacting the bone screws.

Figure 14:
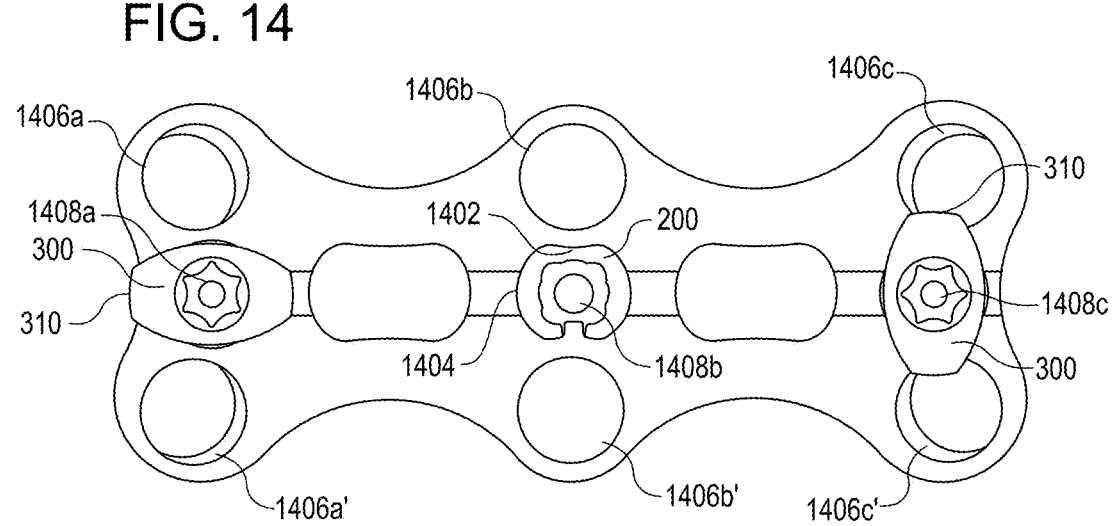
FIG. 14 is a top view of a partially assembled bone plate for receiving three exemplary locking assemblies, showing locks in both the unlocked and locked positions.

FIG. 14 shows a bone plate assembly 1400 in a top plan view, the bone plate assembly employing locks 300 and locking rings 200 in various illustrative states. The bone plate assembly 1400 includes six screw-holes 1406a-c and 1406a'-c' (collectively, 1406), and three through-holes 1408a-c (collectively 1408) for locks. Each through-hole 1408 is disposed adjacent to two respective screw-holes 1406. The screw-holes 1406 are arranged in a polyaxial configuration to permit the insertion of screws (not shown) therein at different angles, in order to achieve improved attachment to bone. For example, the first pair of screw through-holes 1406a, 1406a' are oriented such that screws placed therein would extend toward one another and toward the first end of the bone plate; the second pair of screw through-holes 1406b, 1406b' are oriented downward, and the third pair of screw through-holes 1406c, 1406c' are oriented such that the screws placed therein extend toward one another and toward the second end of the bone plate. In some cases, the screw through-holes can be oriented in various other directions, which can be symmetrical or asymmetrical, in order to direct screws in various other directions.

In the bone plate assembly 1400 shown, a first lock 300 is shown engaged in the first through-hole 1408a and is oriented in an unlocked position, where the overhang 310 of the lock is not obstructing the adjacent screw through-holes 1406a and 1406a'. The second through-hole 1408b is shown without a lock, so as to illustrate one exemplary placement of a locking ring 200 in the counter-bore 1404 around the through-hole 1408b. The locking ring 200 rests in the counter-bore 1404 and is rotationally secured relative to the bone plate assembly 1400 by a counter-bore 1404. The third-through-hole 1408c is shown with an additional lock 300 oriented in a locked position, where the overhang 310 of the additional lock is obstructing both of the adjacent screw through-holes 1406c, 1406c'. Notably, the screw through-holes 1406 can be directly opposite one another across their associated through-hole 1408, as in 1408b and 1406b, 1406b'; or can be substantially opposite one another, with an offset, as in 1408a and 1406a, 1406a'.

Various of the features shown in FIGS. 1-14 may be omitted or modified without deviating from the spirit of the above disclosure. For example, locking mechanisms including the rotating lock (e.g., lock 300, FIG. 3) may be installed in a bone plate by any suitable mechanism that secures the rotating lock to the bone plate while allowing rotation. For example, in some cases, instead of a locking mechanism through-hole or bore (e.g. bore 112, FIG. 1), the locking mechanism may be installed using an undercut and bearing element or flange, or other suitable means.

Figure 15:
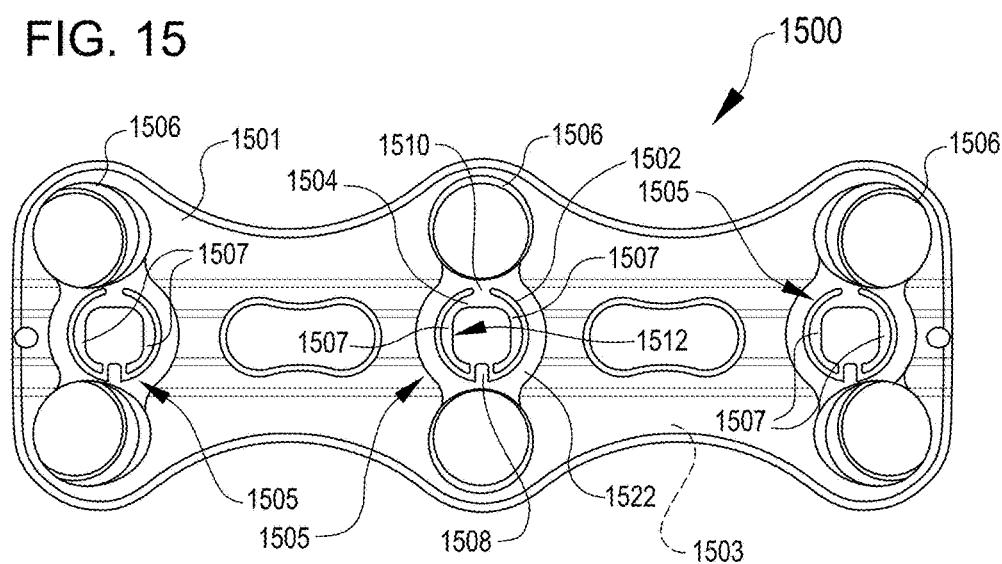
FIG. 15 is a top view of a bone plate according to a fourth example.

FIG. 15 is a top view of a bone plate 1500 according to a fourth example, with a superior surface 1501 of the bone plate visible, where the opposing inferior surface 1503 is configured to attach to two or more vertebrae by a plurality of bone screws. The bone plate 1500 includes a plurality of screw through-holes 1506 sized and shaped to retain bone screws therethrough that can secure the bone plate to the vertebrae. The screw through-holes 1506 can be arranged singly, in pairs (as shown), or in larger sets that are each positioned adjacent to one or more bores 1505 disposed in the superior surface of the bone plate 1500. The bores 1505 may also be positioned in flattened or depressed portions 1522 of the superior surface of the bone plate 1500, although they need not be. In certain embodiments, the depressed portions may be recessed relative to the superior surface and/or may be more planar than other portions of the superior surface, which may or may not have a curvature along its length and/or width. The depressed portions 1522 may minimize potential interference between the bone plate 1500 and the lock while the lock is rotated, and may also allow for the lock to have a lower profile when assembled with the bone plat 1500. These bores 1505 may be blind, or may pass entirely through the bone plate 1500, but generally include a lower surface 1514 that covers at least a portion, if not all, of the bottom of the bore.

The bore geometry can also include a spring element 1504 connected with the side of the bore, separated from the bore sidewall by an arcuate void 1502 that permits the spring element 1504 to flex radially with respect to the bore 1505. The spring element 1504 can be integrally formed with the bone plate 1500, and defined by material removal from the superior surface 1501 of the bone plate. The spring element 1504 may be connected with the bore sidewall by a bridge 1510, or by multiple bridges, and may include one or two, or more, individual cantilevered spring members 1507 that branch to circumscribe at least a portion of the bore 1505. Each of the cantilevered spring members 1507, or the spring element 1504 as a whole, may include flexible C-shaped elements that can flex outward with respect to a center of the bore 1505 when acted upon by a radial force. In addition, one or more positive features 1508 (i.e., tabs or interference members) may protrude from the bore sidewall into the bore 1505. The embodiment of the bone plate 1500 illustrated in FIG. 15 contains three bores 1505 and three sets of closely spaced screw through-holes 1506 positioned adjacent to the respective bores 1505, but alternative bone plates may have more or fewer bores and screw through-holes without deviating from the spirit of this disclosure. Bores 1505 can be formed by any suitable means such as, but not limited to, machining, casting, or 3D printing. According to some embodiments, the bores 1505 can be formed in the bone plate 1500 by a two-step machining process that includes material removal to define the spring element 1504 and material removal to define an undercut 1516 and to separate the spring element 1504 from the lower surface 1514 of the bore. The undercut 1516 can interact with a flanged bottom end of a rotatable lock installed within the bore (see, e.g., FIG. 17, rotatable lock 1700, and flange 1708, below) to facilitate installation and retention of the rotatable lock in the bore. The machining steps may be performed in any suitable order.

Figure 16:
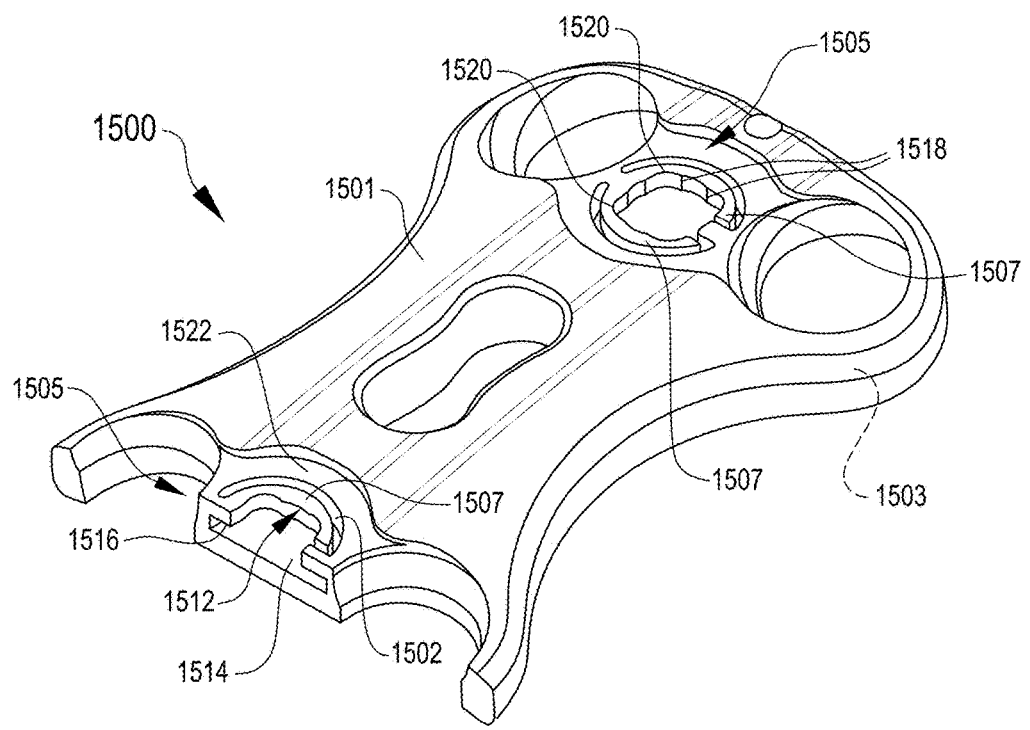
FIG. 16 is a perspective view of the bone plate of FIG. 15, sectioned to show additional detail.

FIG. 16 is a perspective view of the bone plate 1500 of FIG. 15, sectioned to show additional detail. The spring element 1504, as shown, is suspended within the bore 1505 and above the lower surface 1514 with a nonzero clearance, which may be approximately 0.1 mm to 1.0 mm, preferably about 0.3 mm. The undercut 1516 is visible below the bridge 1510, below the spring element 1504, and also below the positive feature(s) 1508, having the same clearance, or a similar clearance, below each part within the bore 1505. The spring element 1504 can further include radial features on an inner surface 1512 including, but not limited to, any suitable number of depressions 1520 separated by any suitable number of ridges 1518. The ridges 1518 may define a circular path that is concentric with and inside the bore 1505, while the depressions 1520 extend outward away from the circular path. According to some embodiments, the depressions 1520 can be located at regular intervals separated by an angle of about 90 degrees, though other angles are possible. In at least one embodiment, there are four depressions 1520 in the inner surface 1512 of each spring element 1504, disposed in pairs that are positioned opposite each other, and which may be but are not necessarily circumferentially equidistant. The depressions 1520 may be arranged so that at least two depressions are located at an angle with respect to each other that matches a rotational angle required to lock the rotatable lock 1700 described below.

Figure 17:
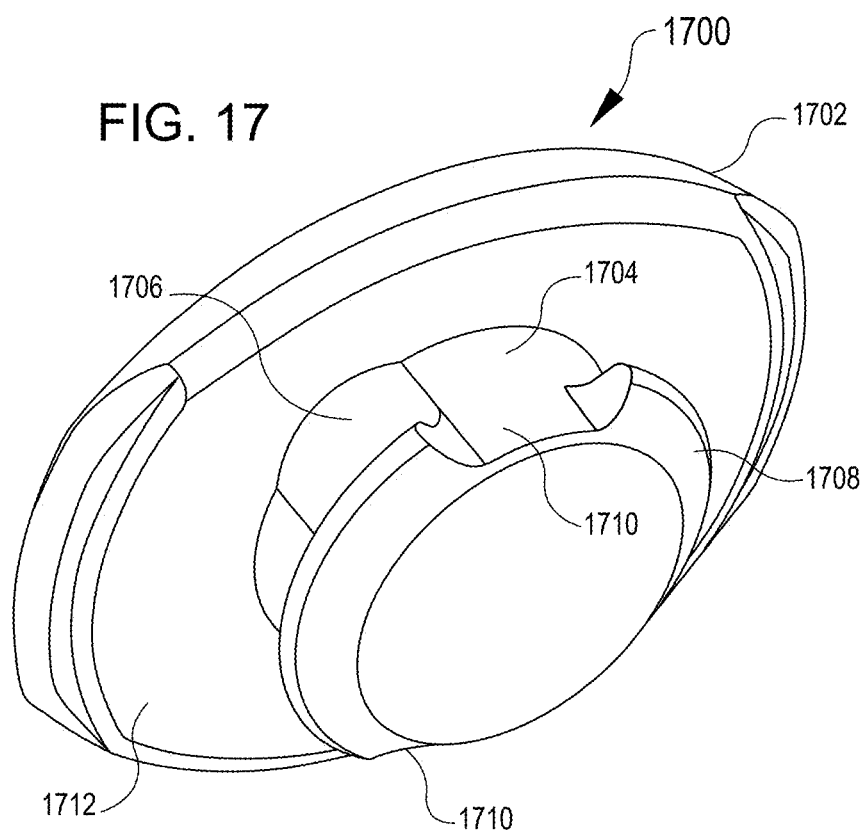
FIG. 17 is a perspective view of a rotatable lock configured to be received in the bone plate of FIG. 15.

FIG. 17 is a perspective view of a rotatable lock 1700 configured to be received in the bone plate 1500 of FIG. 15. Each bore (see, e.g., bores 1505, FIG. 15) is sized to receive a rotatable lock (e.g., lock 300, FIG. 1; or rotatable lock 1700, FIG. 17 below) and to retain the rotatable lock in position longitudinally (or vertically) while permitting it to be turned by a user. The rotatable lock 1700 may share various features with the locks disclosed above, e.g. lock 300 (FIG. 3) including a head portion 1702, shaft 1704, and positive radial features 1706. The rotatable lock 1700 can include a flange 1708 at an end of the shaft 1704 opposite the head portion 1702 that allows the rotatable lock to mate with the bore 1505 by interacting with the undercut 1516. According to some embodiments, the head portion 1702, shaft 1704 (including the radial feature(s) 1706), and flange 1708 can be integrally formed, i.e., formed by a casting or molding process, material removal process, or other suitable process that results in a singular part. Thus, in some embodiments, each of the rotatable lock 1700 and bone plate 1500 can be integrally formed parts, resulting in improvements in long-term durability over multi-part assemblies. In some other embodiments, the rotatable lock 1700 can be an assembly, which may be permanently assembled by way of any suitable permanent assembly process (e.g. welding, sintering, hot interference fitting, or the like).

The head portion 1702 may be elongated in shape, though the specific shape may vary, including oblong circular shapes, ellipses, polygonal shapes, or a combination of the above. The head portion 1702 is sized so that, when the rotatable lock 1700 is mounted to one of the bores (FIG. 15), the head portion 1702 is sufficiently long that, when the rotatable lock is appropriately turned, a bottom side 1712 of the head portion 1702 can cover a backout path of an adjacent bone screw when a bone screw is inserted in any adjacent screw through-hole 1506 (FIG. 15). The length of the head portion 1702 (i.e., in the direction that the head portion extends over the backout path) may vary from about 4.0 mm to about 8.0 mm, and in some embodiments is about 6.05 mm. Conversely, the head portion 1702 is sufficiently narrow, in an orthogonal direction, to allow bone screws to be inserted or removed while the head portion is rotated so as not to block the screw through-holes 1506. The degree of rotation required to lock the rotatable lock 1700 may vary depending on the specific geometry of the bone plate 1500, i.e., the relative positions of the bore 1505 to which the lock is attached, and the locations of the adjacent screw through-holes.

The head portion 1702 can be rotationally symmetrical, or rotationally asymmetrical. The head portion 1702 may be symmetrical for any case where two or more screw through-holes are positioned adjacent and opposite each other across a bore in a bone plate, or where an offset is sufficiently small that a symmetrical head portion would provide coverage over the backout path of screws in the screw through-holes, or where only a single screw through-hole is adjacent the bore. According to some embodiments, the head portion 1702 can be rotationally asymmetrical (e.g., chevron- or kidney-shaped) to provide coverage over screw through-holes where, for example, a pair of screw through-holes are offset with respect to the bore to which the rotatable lock is attached, where only one screw through-hole is adjacent to the heat portion, or in any case where the necessary coverage of the head portion 1702 to match one or more screw through-holes required a particular head geometry.

The radial features 1706 along the shaft 1704 of the rotatable lock 1700 are positioned so that, when the rotatable lock is retained in a bone plate (e.g. bone plate 1500), the radial features 1706 interface with the inner surface 1512 of the spring element 1504. According to various embodiments, at least two depressions 1520 are positioned a suitable angle with respect to each other to define a locked and unlocked position of the rotatable lock 1700, where the locking and unlocking actions are effected by a user twisting the rotatable lock 1700 so that at least one radial feature 1706 from the shaft 1704, by rotating, presses the spring element 1504 outward as the radial feature 1706 mechanically interacts with a ridge 1518 adjacent the first depression 1520. The elastic deformation of the spring element 1504 exerts both a radial and circumferential force on the radial feature 1706 that causes the rotatable lock 1700 to resist being turned. When the rotatable lock 1700 is fully rotated from the unlocked position to the locked position, or vice versa, the radial feature 1706 interacts with a second depression 1520, and the elastic deformation of the spring element 1504 may exert circumferential force on the rotatable lock 1700 to cause it to snap into place in the locked or unlocked position. The rotatable lock 1700 can have one, two, or any suitable number of positive radial features 1706 that are positioned to interact with two, four, or any suitable number of depressions 1520 in the spring element 1504. The locked and unlocked positions correspond to the orientation of the head portion 1702 with respect to the bone plate 1500, and specifically to the positioning of the head portion with respect to any of the screw through-holes 1506 positioned proximate to or adjacent to the bore 1505 in which a provided rotatable lock 1700 is installed. In embodiments resembling the bone plate 1500 shown in FIG. 15, for example, a rotatable lock 1700 installed in the bone plate will be in the unlocked position when the longer dimension of the head portion 1702 is aligned in parallel with the bone plate, and not obstructing any of the screw through-holes 1506. A rotatable lock 1700 installed in the same bone plate 1500 will be in the locked position when the longer dimension of the head portion 1702 is aligned orthogonally with respect to the bone plate, and obstructs the screw through-holes 1506 adjacent to the bore 1505 in which the particular rotatable lock is installed.

At least one, in some cases two, gaps 1710 may be disposed in the flange 1708 to allow for insertion of the rotatable lock 1700 in the bone plate 1500. For example, the cantilevered spring member 1507 of the spring element 1504 can be elastically deformed to permit passage of the flange 1708, but other features of the bore or the spring member may be rigid, such as the bridge 1510 and/or positive feature 1508, and the gap(s) 1710 may be positioned to clear any such rigid features of the bore. According to some embodiments, the gap(s) 1710 are positioned with respect to the geometry of the head portion 1702 so that the rotatable lock 1700 can be inserted into the bone plate 1500 in the same orientation as the unlocked position, and such that rotating the rotatable lock 1700 into the locked position places the solid portions of the flange 1708 underneath the rigid features (e.g., positive feature 1508, bridge 1510), thus providing additional support to the rotatable lock 1700 and preventing removal of the rotatable lock 1700 in the locked position.

Figure 18:
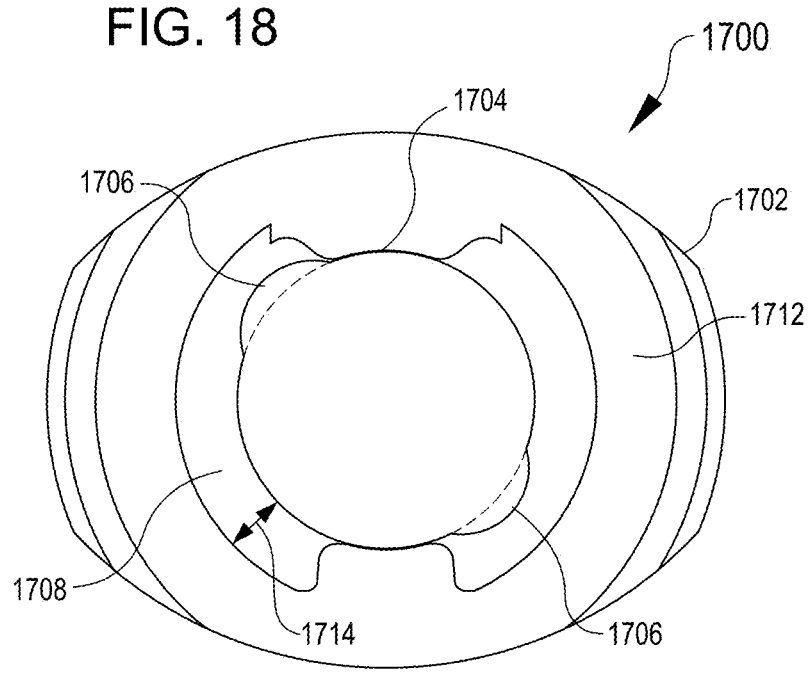
FIG. 18 is a bottom view of the rotatable lock of FIG. 17 showing additional detail.

FIG. 18 is a bottom view of the rotatable lock of FIG. 17 showing additional detail, in which a radial clearance 1714 of the flange 1708 beyond the shaft 1704 is indicated. The radial clearance 1714 can be from about 0.1 mm to about 2.0 mm, more than 2.0 mm, and preferably about 0.5 mm, depending on the size of the bone plate 1500, rotatable lock 1700, and range of flexure of the spring element 1504. The radial clearance 1714 can prevent backout of the rotatable lock 1700 by interference between the flange 1708 and spring element 1504, but may allow snap-fit installation of the rotatable lock 1700 into the bone plate 1500, whereby the flange 1708 forces the spring element 1504 to elastically deform during installation. The flange 1708 can be shaped to resist removal, e.g., having a ramped shape that permits passage through the spring element 1504 when the rotatable lock 1700 is pressed down, but that prevents backout.

Figure 19:
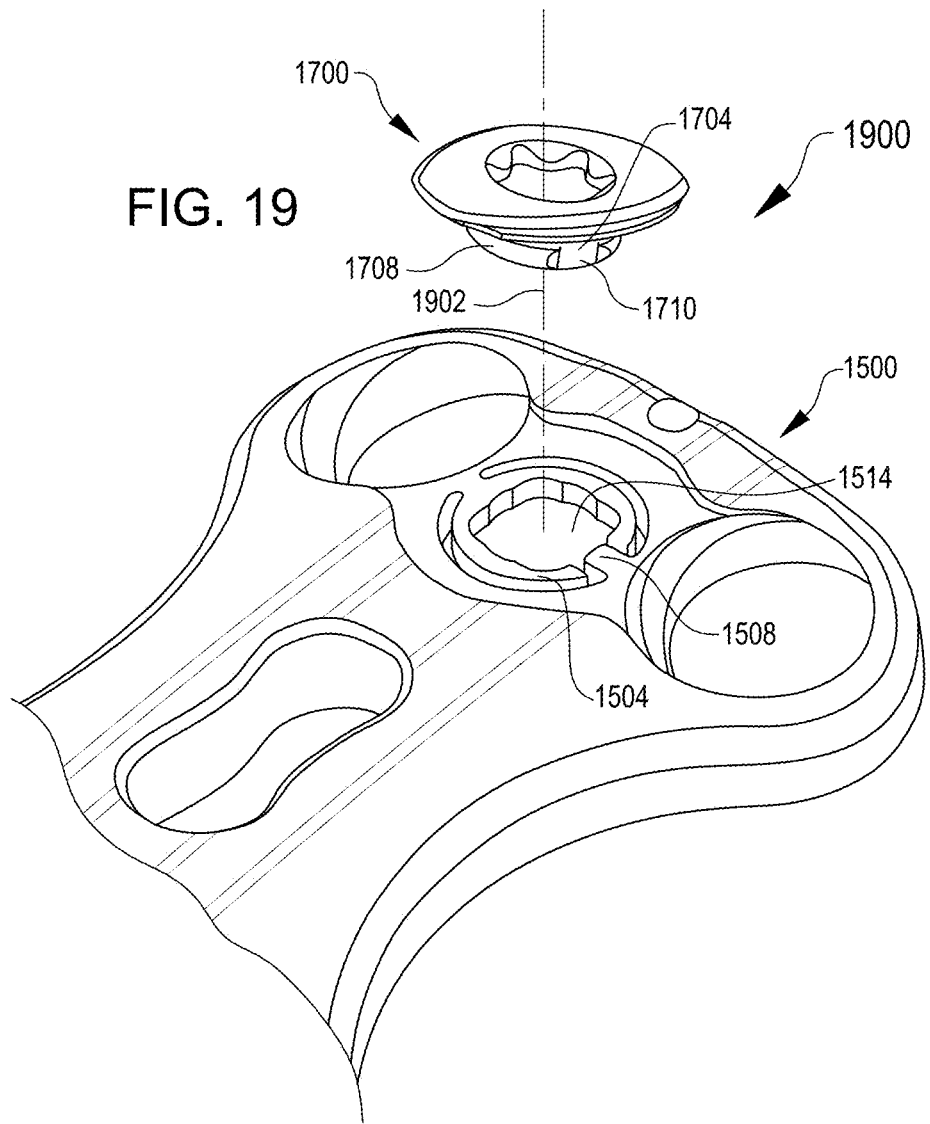
FIG. 19 is a perspective view of an assembly of the bone plate of FIG. 15 and the rotatable lock of FIG. 17.

FIG. 19 is a perspective view of an assembly of the bone plate 1500 of FIG. 15 and rotatable lock 1700 of FIG. 17, in which the shaft 1704 of the rotatable lock 1700 is aligned to be inserted into the bore 1505, so that the flange 1708 snaps into place below the spring element 1504. The rotatable lock 1700 can be a single piece, which may be pressed down into position vertically along a central axis 1902 of the bore 1505. According to various alternative embodiments, the rotatable lock 1700 can be assembled from two or more pieces. For example, the flange 1708 may be placed in the bore 1505 separately and then attached to the shaft 1704. In another alternative embodiment where the bore 1505 includes a through-hole, the flange 1708 may be attached to the shaft 1704 from the opposite side of the bone plate 1500. The geometry of the flange 1708 may vary depending on the specific geometry of the bore 1505 and any spring members or rigid features extending therein.

When assembled, the rotatable lock 1700 and the spring element 1504 of the bone plate 1500 interact to allow a user to repeatedly transition the rotatable lock 1700 between the unlocked and locked positions. When locked, the head portion 1702 of the rotatable lock 1700 blocks a backout path of any installed bone screws inserted in an adjacent screw through-hole, but without exerting direct pressure on the bone screws. This mechanism allows for the bone screws to settle naturally in the bone to which they are implanted, and improves therapeutic outcomes. The ability to readily unlock the rotatable lock 1700 greatly reduces the complexity of revision surgery, and the action of the spring element 1504 provides tactile feedback to a user when locking or unlocking the rotatable lock, improving ease of use during surgery.

Figure 20:
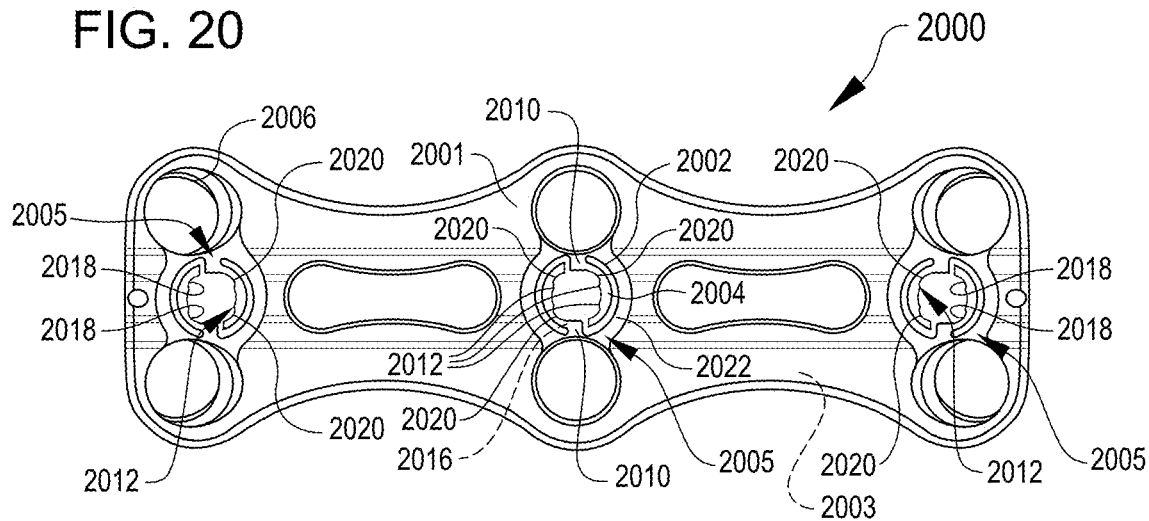
FIG. 20 is a top view of a bone plate according to a fifth example.

FIG. 20 is a top view of a bone plate 2000 according to a fifth example, having a spring member 2004 with different geometry than spring element 1504, but similar functional advantages to those described above. Bone plate 2000 has a superior surface 2001, an opposing inferior surface 2003, and is configured to attach to two or more vertebrae by a plurality of bone screws. The bone plate 2000 includes a plurality of screw through-holes 2006 sized and shaped to retain bone screws therethrough that can secure the bone plate to the vertebrae. The screw through-holes 2006 can be arranged singly, in pairs (as shown), or in larger sets where each set is positioned adjacent to one or more bores 2005 disposed in the superior surface of the bone plate 2000. The bores 2005 may also be positioned in flattened or depressed portions 2022 of the superior surface of the bone plate 2000, although they need not be. These bores 2005 may be blind cavities, or may pass entirely through the bone plate 2000, but generally include a lower surface 2014 that covers at least a portion, if not all, of the bottom of the bore.

Figure 21:
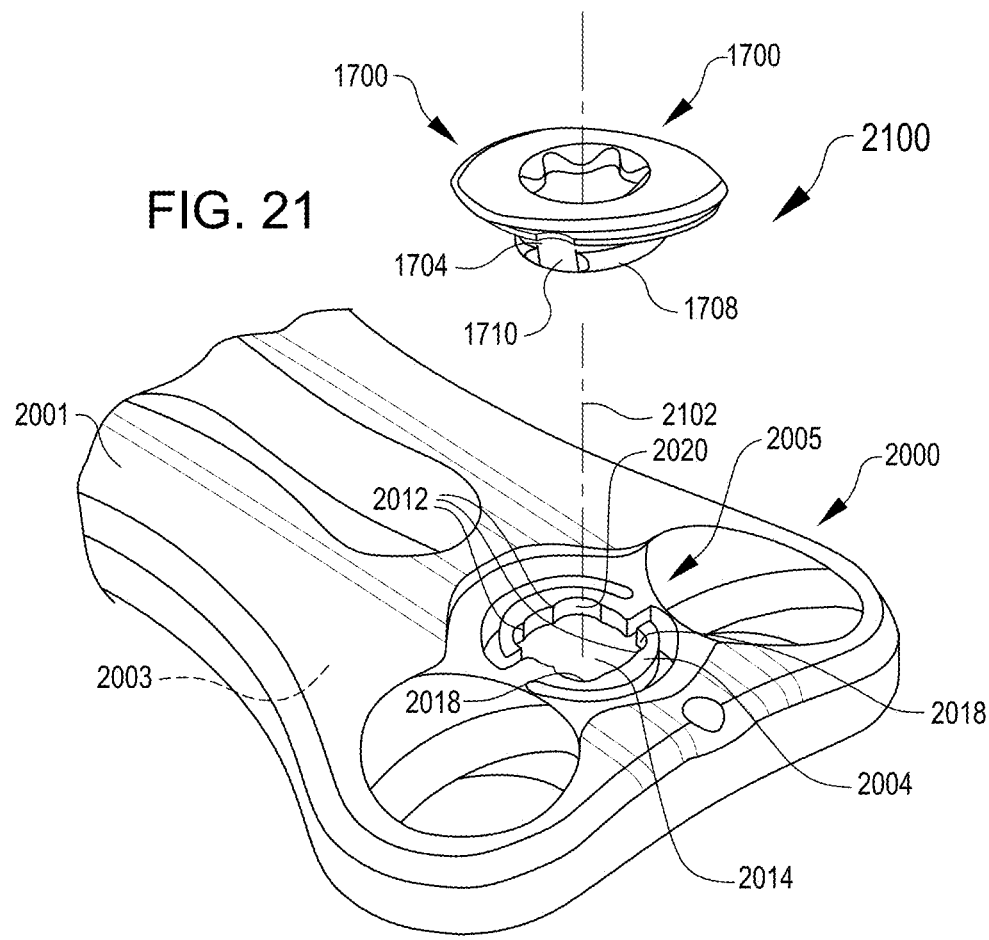
FIG. 21 is a perspective view of an assembly of the bone plate of FIG. 20 and the rotatable lock of FIG. 17.
Figure 22:
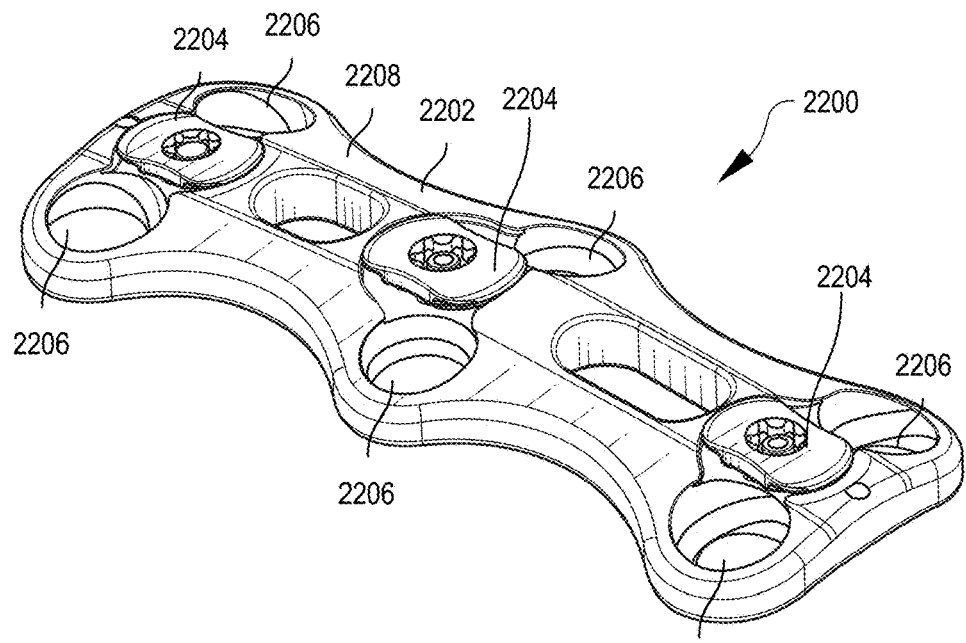
FIG. 22 is a top perspective view of a bone plate according to embodiments.

The bone plate 2000 includes mirror asymmetric spring members 2004 made up of two separate cantilevered springs that, together, define two interior surfaces 2012 having a similar shape to the inner surfaces 1512 described above with reference to FIG. 15 (bone plate 1500). The spring member 2004 can be integrally formed with the bone plate 2000, and defined by material removal from the superior surface 2001 of the bone plate. The interior surfaces 2012 define a plurality of depressions 2020 separated by ridges 1018 that can interact with a rotatable lock, and the spring members 2004 can flex to allow rotation of the rotatable lock 1700. Attachment of a rotatable lock (e.g., rotatable lock 1700, FIG. 17) can be achieved in the manner illustrated in FIG. 21, which is a perspective view of an assembly 2100 of the bone plate of FIG. 20 and rotatable lock of FIG. 17. The rotatable lock 1700 can be pressed directly into the bore 2005 along a central axis 2102 such that the flange 1708 causes deformation of the spring members 2008, which subsequently snap into place, securing the rotatable lock 1700. A gap 1710 in the flange 1708 may be provided to allow the rotatable lock to clear the bridges 2010 supporting the spring members 2008, or any other rigid extensions into the bore 2005.

FIGS. 22-28 illustrate another embodiment of a bone plate assembly 2200 with a bone plate 2202 and at least one rotatable lock 2204.

Figure 27:
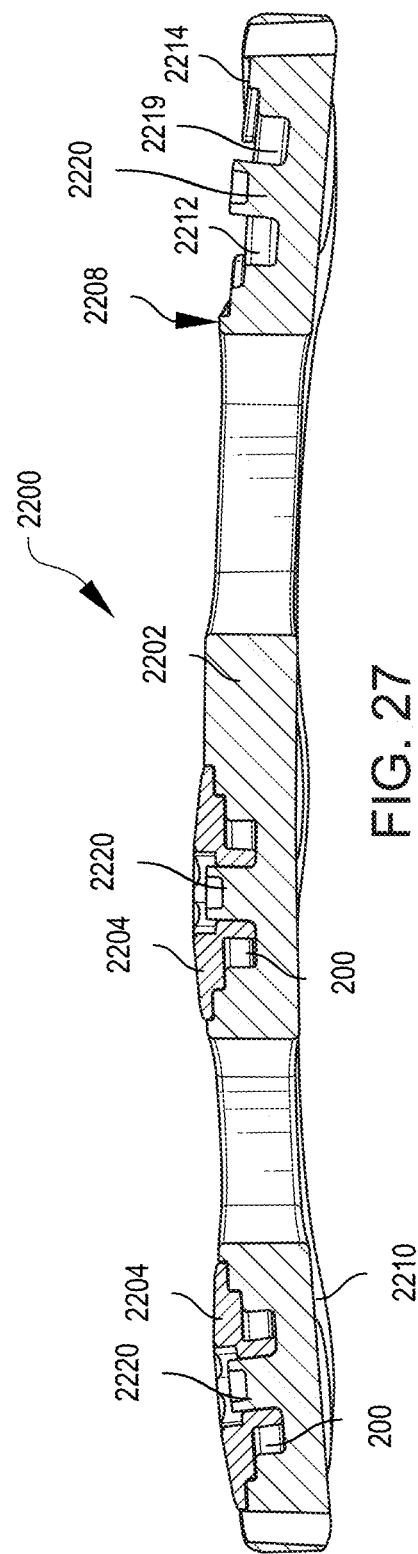
FIG. 27 is a sectional view of the bone plate of FIG. 26.
Figure 28:
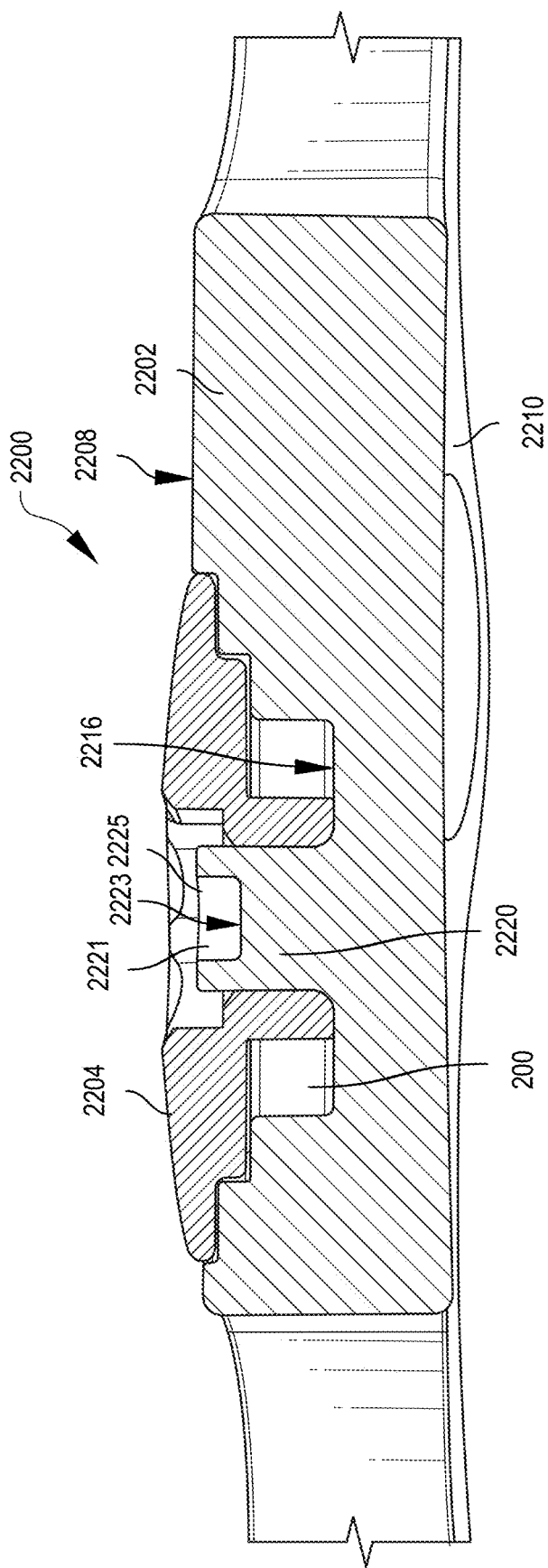
FIG. 28 is a sectional view of a portion of the bone plate of FIG. 26.

Similar to other bone plates described previously, the bone plate 2202 includes one or more screw through-holes 2206 that extend from a superior surface 2208 of the bone plate 2202 to an inferior surface 2210 of the bone plate 2202 (e.g., through a thickness of the bone plate 2202). The screw through-holes 2206 may be provided in various arrangements or patterns on the bone plate 2202 as desired. In certain embodiments, the screw through-hole(s) 2206 are sized and shaped to retain bone screws, which can secure the bone plate 2202 to the vertebrae. As best illustrated in FIGS. 27 and 28, in various embodiments, the bone plate 2202 may have a curvature along its length and/or along its width. In other words, the superior surface 2208 and/or the inferior surface 2210 may be non-planar surfaces. In other embodiments, the bone plate 2202 may have various other shapes or profiles as desired.

As best illustrated in FIGS. 23, 24, 27, and 28, the bone plate 2202 also includes one or more locking cavities 2212 that are positioned adjacent to one or more of the screw through-holes 2206. As discussed in detail below, each locking cavity 2212 may accommodate a corresponding rotatable lock 2204 that can selectively cover or uncover a bone screw in an adjacent screw through-hole 2206 (e.g., the prevent backout or allow for removal). In various embodiments, the locking cavities 2212 may be provided in a flattened or depressed portion 2214 of the superior surface 2208. Each locking cavity 2212 provided in a corresponding depressed portion 2214 may minimize an extent by which a rotatable lock 2204 may project away from the bone plate 2202 when it is positioned in the locking cavity 2212. Each locking cavity 2212 in a corresponding depressed portion 2214 may also facilitate rotation of the lock 2204 between a locked position and an unlocked position (e.g., covering or uncovering the screw through-hole 2206).

Figure 23:
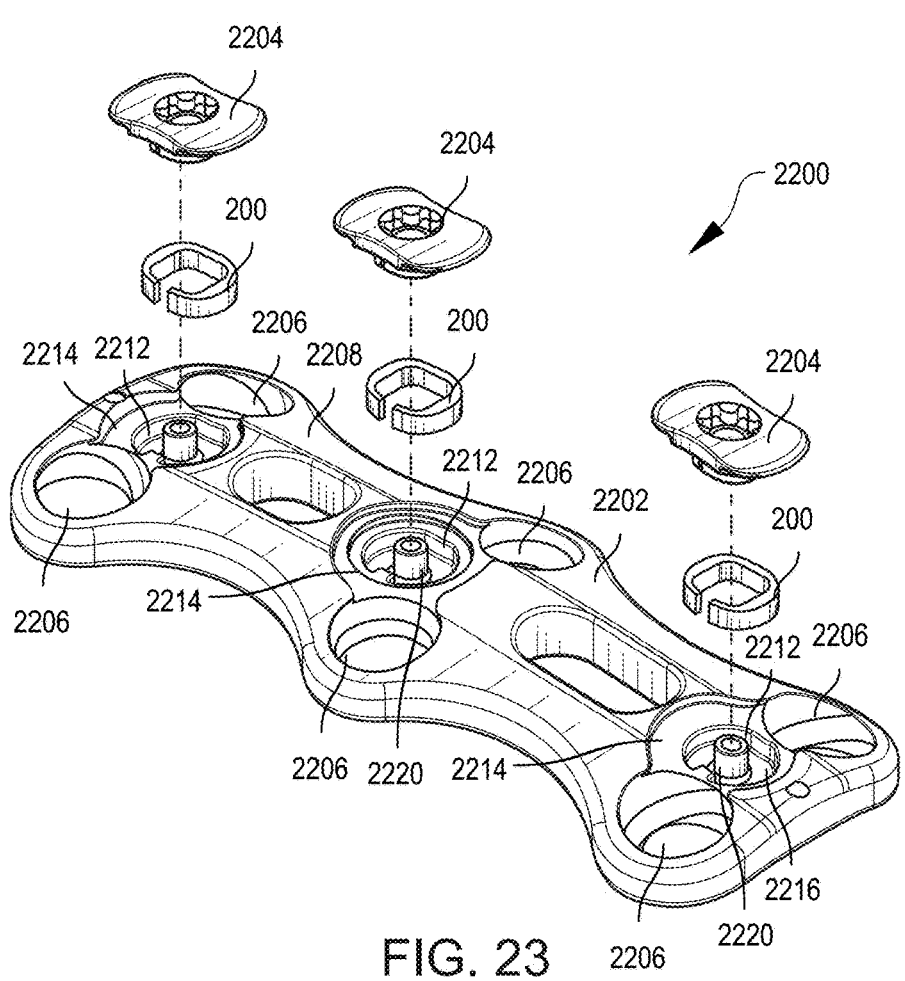
FIG. 23 is an exploded view of the bone plate of FIG. 22.
Figure 24:
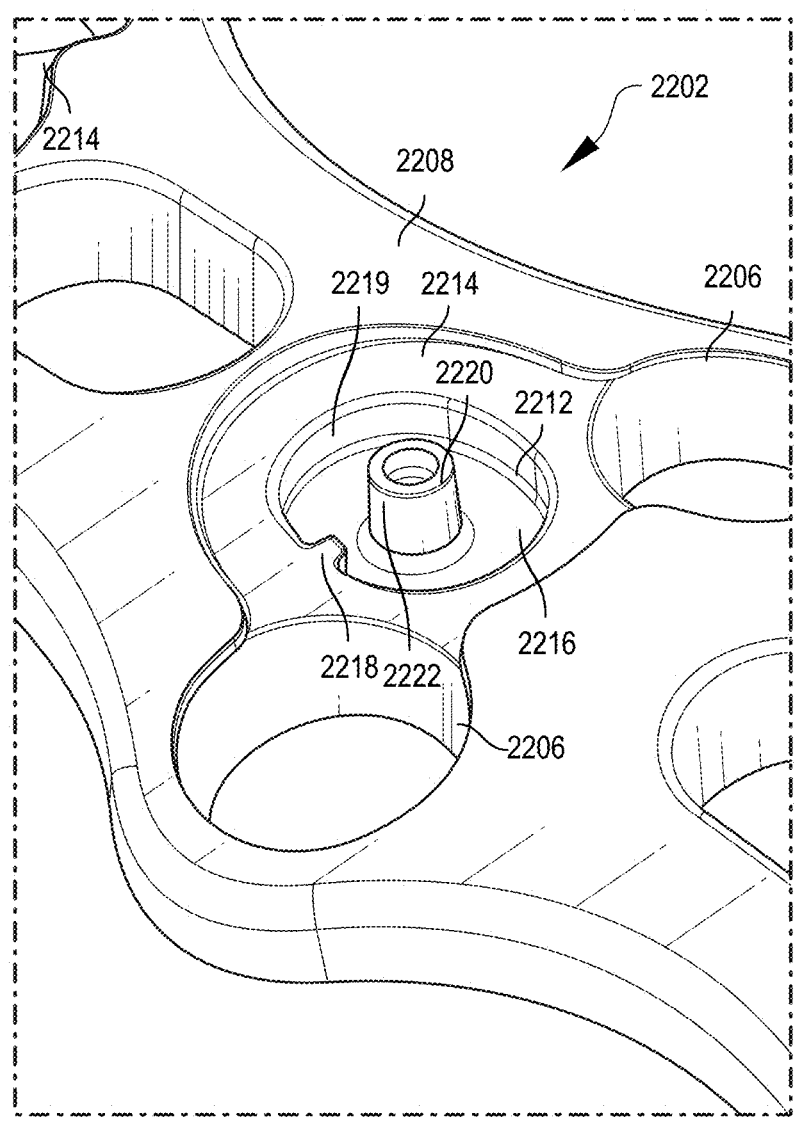
FIG. 24 is a perspective view of a portion of the bone plate of FIG. 22.

The locking cavities 2212 are defined in the superior surface 2208 and are blind, meaning that they do not extend all the way through the bone plate 2202 to the inferior surface 2210. As best illustrated in FIGS. 23 and 24, each locking cavity 2212 includes a bottom surface 2216 that is recessed relative to the superior surface 2208 and a sidewall surface 2219 extending from the superior surface 2208 to the bottom surface 2216. In certain embodiments, each locking cavity 2212 may include a locking feature 2218 that is configured to interact with the locking ring 200 in the locking cavity 2212. In various embodiments, the locking feature 2218 may extend from the sidewall surface 2219, although it need not in other embodiments.

In various embodiments, each locking cavity 2212 includes a post 2220 extending upwards from the bottom surface 2216. The post 2220 may be integrally formed with the bone plate 2202 (e.g., the post 2220 and the bone plate 2202 are a single, monolithic structure) or may be a separate component that is secured in the locking cavity 2212 via various suitable mechanisms or devices as desired. In certain cases, the post 2220 may be centered within the locking cavity 2212, although it need not be in other embodiments. As discussed in detail below, the rotatable locks 2204 may be supported on the posts 2220 within each locking cavity 2212, and each lock 2204 may be rotatable while supported on the corresponding post 2220. In some cases, the shoulder 304 of the rotatable lock 2204 may optionally contact the bottom surface 2216 of the locking cavity 2212 when the rotatable lock 2204 is supported on the post 2220, although it need not in other embodiments. In various embodiments, an outer surface 2222 of each post 2220 may include surface features to facilitate retention of the lock 2204 on the post 2220. As one non-limiting example, the outer surface 2222 may have a profile that frictionally minimizes or prevents movement axially along the post 2220 (e.g., without deformation of the post 2220) while allowing for rotation of the lock 2204 on the post 2220. In other embodiments, other features on the post 2220 may be utilized as desired. As another non-limiting example, a cap may engage the end of the post 2220 such that the lock 2204 is retained on the post 2220 between the bottom surface 2216 and the cap. In some embodiments, a top of the post 2220 includes a recess 2221. The recess 2221 includes a bottom recess surface 2223 and a side recess surface 2225.

Figure 25:
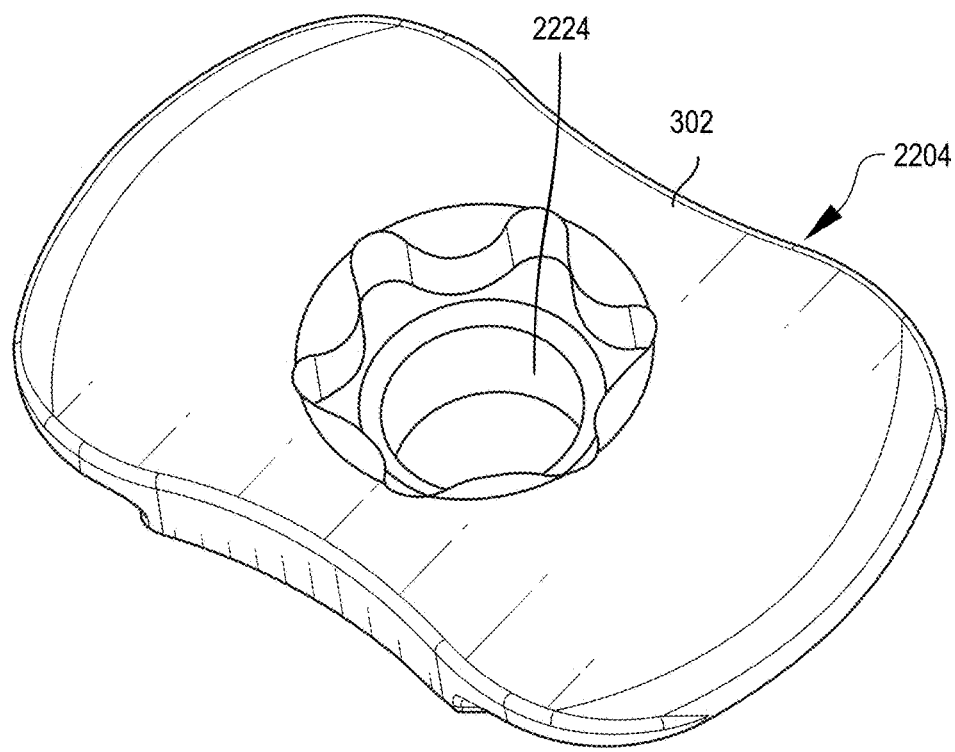
FIG. 25 is a top perspective view of a lock of the bone plate of FIG. 22.
Figure 26:
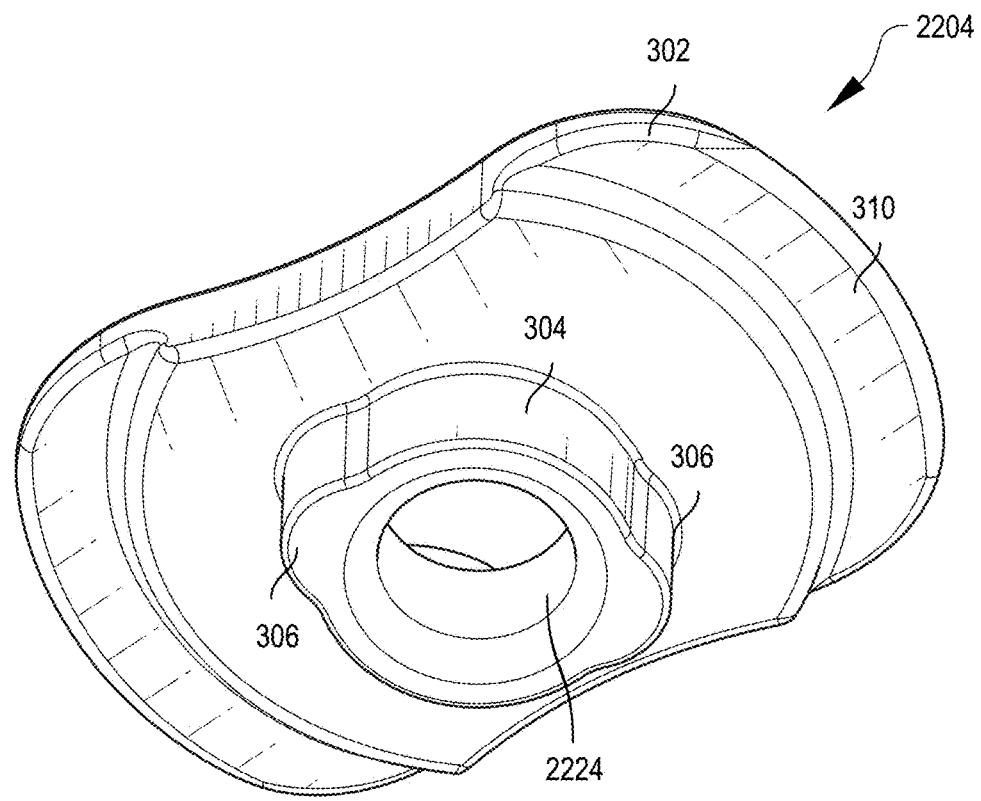
FIG. 26 is a bottom perspective view of the lock of FIG. 25.

Referring to FIGS. 25 and 26, the lock 2204 is substantially similar to the lock 300 except that the lock 2204 does not include the shaft 308. In addition, a shape of the head section 302 of the lock 2204 is different compared to the head section 302 of the lock 300. In the embodiment of FIGS. 25 and 26, a central bore 2224 may extend through the head section 302 and the shoulder 304. When the lock 2204 is assembled with the bone plate 2202, the post 2220 may at least partially extend through the central bore 2224, as illustrated, for example, in FIGS. 27 and 28. In certain embodiments, when the lock 2204 is positioned on the post 2220, the post 2220 may optionally not extend completely through the lock 2204 (e.g., the lock 2204 may be an outermost portion). In certain aspects, and compared to the lock 300, the lock 2204 on the post 2220 of the bone plate 2202 may reduce the number of parts needed to assemble the bone plate assembly 2200, may reduce the number of moving parts on the bone plate assembly 2200, and/or may provide a location with improved strength for supporting the lock 2204 and allowing for rotation of the lock 2204.

Other embodiments of bone plate assemblies and/or components of bone plate assemblies may include various combinations or sub-combinations of features described herein. Alternative designs may include bone plates having any suitable number of associated locks and screw-holes. Screw through-holes may be arranged in pairs around a lock having two overhanging portions, in triplicate around a lock having three overhanging portions, in quadruplicate around a lock having four overhanging portions, or in any other suitable, comparable arrangement, provided that the associated locking features thereof allow the lock to rotate between unlocked and locked positions at various locking angles as appropriate. For example, where a lock has two associated screw through-holes, an appropriate locking angle may be approximately 90 degrees. Where a lock has three associated screw through-holes, an appropriate locking angle may be approximately 60 degrees. Where a lock has four associated screw through-holes, an appropriate locking angle may be approximately 45 degrees, and so on.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below A collection of exemplary embodiments are provided below, including at least some explicitly enumerated as "Illustrations" providing additional description of a variety of example embodiments in accordance with the concepts described herein. These examples are not meant to be mutually exclusive, exhaustive, or restrictive; and the disclosure not limited to these examples but rather encompasses all possible modifications and variations within the scope of the issued claims and their equivalents.

Illustration 1. A bone plate assembly comprising: a bone plate comprising: a superior surface; an inferior surface; at least one screw through-hole configured to receive a bone screw; and a locking cavity defined in the superior surface, the locking cavity comprising a bottom surface that is recessed relative to the superior surface and a post extending upwards from the bottom surface; and a rotatable lock supported on the post, wherein the rotatable lock is rotatable while supported on the post.

Illustration 2. The bone plate assembly of any preceding or subsequent illustrations or combination of illustrations, wherein the locking cavity is a first locking cavity of a plurality of locking cavities and the post is a first post of a plurality of posts, and wherein each locking cavity comprises a post.

Illustration 3. The bone plate assembly of any preceding or subsequent illustrations or combination of illustrations, wherein the rotatable lock comprises a head portion, a shoulder, and a central bore extending through the head portion and the shoulder, and wherein the rotatable lock is supported on the post such that the post at least partially extends into the central bore.

Illustration 4. The bone plate assembly of any preceding or subsequent illustrations or combination of illustrations, wherein the rotatable lock is rotatable between a locked position and an unlocked position, wherein, in the locked position, the rotatable lock at least partially covers the at least one screw through-hole, and wherein, in the unlocked position, the rotatable lock does not cover the at least one screw through-hole.

Illustration 5. The bone plate assembly of any preceding or subsequent illustrations or combination of illustrations, wherein the locking cavity is provided in a depressed portion of the superior surface of the bone plate.

Illustration 6. The bone plate assembly of any preceding or subsequent illustrations or combination of illustrations, further comprising at least one bone screw, wherein the at least one bone screw is removably positioned within the at least one screw through-hole.

Illustration 7. The bone plate assembly of any preceding or subsequent illustrations or combination of illustrations, wherein the locking cavity further comprises: a sidewall surface extending between the bottom surface of the locking cavity and the superior surface of the bone plate; and a locking feature extending from the sidewall surface within the locking cavity.

Illustration 8. The bone plate assembly of any preceding or subsequent illustrations or combination of illustrations, wherein the post is centered within the locking cavity.

Illustration 9. The bone plate assembly of any preceding or subsequent illustrations or combination of illustrations, wherein the post is monolithically formed with the bone plate.

Illustration 10. A bone plate assembly comprising: a bone plate comprising: a superior surface; at least one screw through-hole configured to receive a bone screw; a blind locking cavity defined in the superior surface; and a post within the locking cavity; and a lock supported on the post such that the lock is at least partially within the locking cavity.

Illustration 11. The bone plate assembly of any preceding or subsequent illustrations or combination of illustrations, wherein the lock is rotatable on the post between a locked position and an unlocked position, wherein, in the locked position, the rotatable lock at least partially covers the at least one screw through-hole, and wherein, in the unlocked position, the lock does not cover the at least one screw through-hole.

Illustration 12. The bone plate assembly of any preceding or subsequent illustrations or combination of illustrations, wherein the at least one screw through-hole comprises two screw through-holes, wherein, in the locked position, the rotatable lock at least partially covers each of the two screw through-holes, and wherein, in the unlocked position, the lock does not cover either of the two screw through-holes.

Illustration 13. The bone plate assembly of any preceding or subsequent illustrations or combination of illustrations, wherein the locking cavity is a first locking cavity of a plurality of locking cavities and the post is a first post of a plurality of posts, and wherein each locking cavity comprises a post.

Illustration 14. The bone plate assembly of any preceding or subsequent illustrations or combination of illustrations, wherein the superior surface is non-planar.

Illustration 15. The bone plate assembly of any preceding or subsequent illustrations or combination of illustrations, wherein the locking cavity comprises: a bottom surface; a sidewall surface extending between the bottom surface of the locking cavity and the superior surface of the bone plate; and a locking feature extending from the sidewall surface within the locking cavity.

Illustration 15a. The bone plate assembly of any preceding or subsequent illustrations or combination of illustrations, wherein the lock comprises a shoulder and a head portion, wherein the shoulder comprises a radial feature such that the shoulder is non-circular, and wherein the locking feature is configured to selectively abut the radial feature such that the lock is restricted to a partial arc of rotation on the post.

Illustration 16. The bone plate assembly of any preceding or subsequent illustrations or combination of illustrations, wherein the post is monolithically formed with the bone plate.

Illustration 17. A bone plate assembly comprising a bone plate, the bone plate comprising: a superior surface; an inferior surface; at least one screw through-hole configured to receive a bone screw; a locking cavity defined in the superior surface, wherein the locking cavity comprises: a bottom surface that is recessed relative to the superior surface; a sidewall surface extending from the bottom surface to the superior surface; a post within the locking cavity; and a locking feature extending from the sidewall surface into the locking cavity.

Illustration 18. The bone plate assembly of any preceding or subsequent illustrations or combination of illustrations, further comprising a lock supported on the post such that the lock is at least partially within the locking cavity.

Illustration 19. The bone plate assembly of any preceding or subsequent illustrations or combination of illustrations, wherein the lock is rotatable on the post between a locked position and an unlocked position, wherein, in the locked position, the rotatable lock at least partially covers the at least one screw through-hole, and wherein, in the unlocked position, the lock does not cover the at least one screw through-hole.

Illustration 20. The bone plate assembly of any preceding or subsequent illustrations or combination of illustrations, wherein the at least one screw through-hole comprises two screw through-holes, wherein, in the locked position, the rotatable lock at least partially covers each of the two screw through-holes, and wherein, in the unlocked position, the lock does not cover either of the two screw through-holes.

Illustration 21. The bone plate assembly of any preceding or subsequent illustrations or combination of illustrations, wherein the locking feature is configured to abut a surface of a lock such that the lock is restricted to a partial arc of rotation.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A bone plate assembly comprising:
   a bone plate comprising:
      a superior surface;
      an inferior surface;
      at least one screw through-hole configured to receive a bone screw; and
      a locking cavity defined in the superior surface, the locking cavity comprising a bottom surface that is recessed relative to the superior surface, a sidewall surface extending from the bottom surface to the superior surface and defining a perimeter of the locking cavity, and a post extending upwards from the bottom surface, wherein a top of the post opposite from the bottom surface of the locking cavity comprises a recess comprising a bottom recess surface and a side recess surface extending from the bottom recess surface to the top of the post; and
   a rotatable lock supported on the post, wherein the rotatable lock is rotatable while supported on the post, wherein the rotatable lock comprises a head section and a shoulder, wherein the head section comprises an outer surface of the rotatable lock, wherein the rotatable lock is supported on the post such that the top of the post is recessed within the rotatable lock relative to the outer surface of the rotatable lock, and wherein the head section of the rotatable lock is outside of the locking cavity and the shoulder of the rotatable lock is within the locking cavity and contacting the bottom surface of the locking cavity, wherein a maximum dimension of the head section is greater than a maximum dimension of the shoulder.

2. The bone plate assembly of claim 1, wherein the locking cavity is a first locking cavity of a plurality of locking cavities and the post is a first post of a plurality of posts, and wherein each locking cavity comprises a post.

3. The bone plate assembly of claim 1, wherein the rotatable lock is rotatable between a locked position and an unlocked position, wherein, in the locked position, the rotatable lock at least partially covers the at least one screw through-hole, and wherein, in the unlocked position, the rotatable lock does not cover the at least one screw through-hole.

4. The bone plate assembly of claim 1, further comprising at least one bone screw, wherein the at least one bone screw is removably positioned within the at least one screw through-hole.

5. The bone plate assembly of claim 1, wherein the locking cavity further comprises:
   a locking feature extending from the sidewall surface within the locking cavity and configured to engage with the rotatable lock.

6. The bone plate assembly of claim 1, wherein the post is monolithically formed with the bone plate.

7. A bone plate assembly comprising:
   a bone plate comprising:
      a superior surface;
      an inferior surface;
      at least one screw through-hole configured to receive a bone screw;
      a blind locking cavity defined in the superior surface, the blind locking cavity comprising a bottom surface and a sidewall surface extending from the bottom surface to the superior surface, wherein the bottom surface is recessed relative to the superior surface; and
      a post within the locking cavity, wherein a top of the post opposite from the superior surface of the blind locking cavity comprises a recess comprising a bottom recess surface and a side recess surface extending from the bottom recess surface to the top of the post; and
   a lock supported on the post such that the lock is at least partially within the locking cavity, wherein the lock comprises a head section, a shoulder, and a central bore extending through the head section and the shoulder, wherein the head section comprises an outer surface of the lock, wherein the lock is supported on the post such that the post is within the central bore and the top of the post is within the central bore between the outer surface and the shoulder of the lock, and wherein the head section of the lock is outside of the locking cavity and the shoulder of the lock is within the locking cavity and contacting the bottom surface of the locking cavity, wherein a maximum dimension of the head section is greater than a maximum dimension of the shoulder.

8. The bone plate assembly of claim 7, wherein the lock is rotatable on the post between a locked position and an unlocked position, wherein, in the locked position, the rotatable lock at least partially covers the at least one screw through-hole, and wherein, in the unlocked position, the lock does not cover the at least one screw through-hole.

9. The bone plate assembly of claim 8, wherein the at least one screw through-hole comprises two screw through-holes, wherein, in the locked position, the rotatable lock at least partially covers each of the two screw through-holes, and wherein, in the unlocked position, the lock does not cover either of the two screw through-holes.

10. The bone plate assembly of claim 7, wherein the locking cavity is a first locking cavity of a plurality of locking cavities and the post is a first post of a plurality of posts, and wherein each locking cavity comprises a post.

11. The bone plate assembly of claim 7, wherein the locking cavity comprises:
   a locking feature extending from the sidewall surface within the locking cavity.

12. The bone plate assembly of claim 11, wherein the shoulder of the lock comprises a radial feature such that the shoulder is non-circular, and wherein the locking feature is configured to selectively abut the radial feature such that the lock is restricted to a partial arc of rotation on the post.

13. The bone plate assembly of claim 7, wherein the post is monolithically formed with the bone plate.

14. A bone plate assembly comprising a bone plate, the bone plate comprising:
   a superior surface;
   an inferior surface;
   at least one screw through-hole configured to receive a bone screw;
   a locking cavity defined in the superior surface, wherein the locking cavity comprises:
      a bottom surface that is recessed relative to the superior surface;

a sidewall surface extending from the bottom surface to the superior surface and defining a perimeter of the locking cavity;

a post within the locking cavity, wherein a top of the post opposite from the bottom surface of the locking cavity comprises a recess comprising a bottom recess surface and a side recess surface extending from the bottom recess surface to the top of the post; and a locking feature extending from the sidewall surface into the locking cavity; and a rotatable lock supported on the post, wherein the rotatable lock is rotatable while supported on the post, wherein the rotatable lock comprises a head section, a shoulder, and a central bore, wherein the head section comprises an outer surface of the rotatable lock, wherein the rotatable lock is supported on the post such that the top of the post is within the central bore and recessed relative to the outer surface of the rotatable lock, wherein the shoulder is configured to selectively engage the locking feature, and wherein the head section of the rotatable lock is outside of the locking cavity and the shoulder of the rotatable lock is within the locking cavity and contacting the bottom surface of the locking cavity.

15. The bone plate assembly of claim 14, wherein the locking feature is configured to abut a surface of the shoulder of the rotatable lock such that the rotatable lock is restricted to a partial arc of rotation.

16. The bone plate assembly of claim 14, wherein the rotatable lock is rotatable on the post between a locked position and an unlocked position, wherein, in the locked position, the rotatable lock at least partially covers the at least one screw through-hole, and wherein, in the unlocked position, the lock does not cover the at least one screw through-hole.

17. The bone plate assembly of claim 16, wherein the at least one screw through-hole comprises two screw through-holes, wherein, in the locked position, the rotatable lock at least partially covers each of the two screw through-holes, and wherein, in the unlocked position, the lock does not cover either of the two screw through-holes.

* * * * *